US008394356B2

(12) United States Patent
McMurry et al.

(10) Patent No.: US 8,394,356 B2
(45) Date of Patent: *Mar. 12, 2013

(54) DIAGNOSTIC IMAGING CONTRAST AGENTS WITH EXTENDED BLOOD RETENTION

(75) Inventors: Thomas J. McMurry, Winchester, MA (US); Hironao Sijiki, Gifu (JP); Daniel M. Scott, Weston, MA (US); Randall B. Lauffer, Brookline, MA (US)

(73) Assignee: Lantheus Medical Imaging, Inc., North Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/220,103

(22) Filed: Aug. 29, 2011

(65) Prior Publication Data

US 2012/0107249 A1 May 3, 2012

Related U.S. Application Data

(63) Continuation of application No. 11/472,842, filed on Jun. 22, 2006, now Pat. No. 8,017,105, which is a continuation of application No. 10/755,507, filed on Jan. 12, 2004, now Pat. No. 7,229,606, which is a continuation of application No. 10/034,522, filed on (Continued)

(51) Int. Cl.
*A61B 5/055* (2006.01)
*A61B 5/05* (2006.01)

(52) U.S. Cl. .............. 424/9.364; 424/9.365; 424/9.36; 424/9.3; 600/410; 600/420

(58) Field of Classification Search .............. 424/9.3, 424/9.36, 9.364, 9.365; 600/410, 420
See application file for complete search history.

(56) References Cited

U.S. PATENT DOCUMENTS

| 3,632,637 | A | 1/1972 | Martell |
| 4,150,047 | A | 4/1979 | Coe et al. |
| 4,308,249 | A | 12/1981 | Frank et al. |
| 4,331,647 | A | 5/1982 | Goldenberg |
| 4,352,751 | A | 10/1982 | Wieder et al. |
| 4,361,544 | A | 11/1982 | Goldenberg |
| 4,401,647 | A | 8/1983 | Krohn et al. |
| 4,472,509 | A | 9/1984 | Gansow et al. |
| 4,615,879 | A | 10/1986 | Runge et al. |
| 4,639,365 | A | 1/1987 | Sherry |
| 4,647,447 | A | 3/1987 | Gries et al. |
| 4,687,658 | A | 8/1987 | Quay |
| 4,714,607 | A | 12/1987 | Klaveness |
| 4,746,507 | A | 5/1988 | Quay |
| 4,834,964 | A | 5/1989 | Rosen |
| 4,859,451 | A | 8/1989 | Quay et al. |
| 4,880,008 | A | 11/1989 | Lauffer |
| 4,885,363 | A | 12/1989 | Tweedle et al. |
| 4,899,755 | A | 2/1990 | Lauffer et al. |
| 4,957,939 | A | 9/1990 | Gries et al. |
| 4,963,344 | A | 10/1990 | Gries et al. |
| 4,980,502 | A | 12/1990 | Felder et al. |
| 5,017,359 | A | 5/1991 | Nicolau et al. |
| 5,078,986 | A | 1/1992 | Bosworth et al. |
| 5,091,169 | A | 2/1992 | Rocklage et al. |
| 5,094,848 | A | 3/1992 | Brixner |
| 5,223,243 | A | 6/1993 | Rocklage et al. |
| 5,250,285 | A | 10/1993 | Lauffer et al. |
| 5,314,679 | A | 5/1994 | Lewis et al. |
| 5,318,769 | A | 6/1994 | Bacon et al. |
| 5,318,771 | A | 6/1994 | Lauffer et al. |
| 5,358,704 | A | 10/1994 | Desreux et al. |
| 5,362,475 | A | 11/1994 | Gries et al. |
| 5,380,519 | A | 1/1995 | Schneider et al. |
| 5,385,719 | A | 1/1995 | Unger et al. |
| 5,407,659 | A | 4/1995 | Deutsch et al. |
| 5,474,756 | A | 12/1995 | Tweedle et al. |
| 5,487,390 | A | 1/1996 | Cohen et al. |
| 5,505,932 | A | 4/1996 | Grinstaff et al. |
| 5,525,338 | A | 6/1996 | Goldenberg |
| 5,545,395 | A | 8/1996 | Tournier et al. |
| 5,573,752 | A | 11/1996 | Ranganathan et al. |
| 5,635,180 | A | 6/1997 | Morgan, Jr. et al. |
| 5,649,537 | A | 7/1997 | Anelli et al. |
| 5,660,814 | A | 8/1997 | Uggeri et al. |
| 5,674,470 | A | 10/1997 | Tweedle et al. |
| 5,725,840 | A | 3/1998 | Klaveness et al. |
| 5,846,519 | A | 12/1998 | Tweedle et al. |
| 6,307,074 | B1 | 10/2001 | Brocchetta et al. |
| 6,342,598 | B1 | 1/2002 | Anelli et al. |

(Continued)

FOREIGN PATENT DOCUMENTS

| AU | 8633082 | 1/1983 |
| CA | 2139374 | 7/1995 |

(Continued)

OTHER PUBLICATIONS

Office Action in Mexican Patent Appl. 2005/011988 dated Jun. 3, 2008.
"Phenolic derivatives of (hydroxyalkyl)alky-lenediamineacetic acids and their salts" *Chemical Abstracts*, 1978, 89:561, Abstract No. 215057x.
Bagley et al., "Distribution of Intravenously Administered Ferrioxamine-59 and Ferric N,N'-Ethylenebis (βImino-2-Hydroxy-5-Chlorophenylacetate) in Rats", *Proc. Soc. Exptl. Biol. Med.*, 1968, 127:798-801.
Barnhart et al., "Is there Stereospecificity in Hepatic Uptake of Phenyl-derivatized Contrast Agents?" 1993, *Contrast Media Research*.

(Continued)

*Primary Examiner* — Michael G Hartley
*Assistant Examiner* — Leah Schlientz
(74) *Attorney, Agent, or Firm* — Fish & Richardson P.C.

(57) ABSTRACT

The present invention relates to contrast agents for diagnostic imaging with prolonged blood retention. In particular, this invention relates to novel compounds that are characterized by an image enhancing moiety (IEM); a protein plasma binding moiety (PPBM); and a blood half-life extending moiety (BHEM). This invention also relates to pharmaceutical compositions comprising these compounds and to methods of using the compounds and compositions for blood half-life extension and contrast enhancement of diagnostic imaging.

107 Claims, 1 Drawing Sheet

Related U.S. Application Data

Dec. 20, 2001, now Pat. No. 6,676,929, which is a continuation of application No. 08/875,365, filed as application No. PCT/US96/00164 on Jan. 16, 1996, now abandoned, which is a continuation-in-part of application No. 08/382,317, filed on Feb. 1, 1995, now abandoned.

(56) References Cited

U.S. PATENT DOCUMENTS

| | | | |
|---|---|---|---|
| 6,461,588 | B1 | 10/2002 | Anelli et al. |
| 6,479,681 | B2 | 11/2002 | Brocchetta et al. |
| 6,652,834 | B2 | 11/2003 | Anelli et al. |
| 6,652,835 | B1 | 11/2003 | Lauffer et al. |
| 7,011,815 | B2 * | 3/2006 | McMurry et al. ............ 424/9.36 |
| 7,229,606 | B2 * | 6/2007 | McMurry et al. .......... 424/9.364 |

FOREIGN PATENT DOCUMENTS

| | | |
|---|---|---|
| DE | 2606721 | 9/1976 |
| DE | 3129906 | 2/1983 |
| DE | 3401052 | 7/1984 |
| DE | 0450742 | 10/1991 |
| EP | 0133603 | 2/1985 |
| EP | 0165728 | 12/1985 |
| EP | 0230893 | 8/1987 |
| EP | 0232751 | 8/1987 |
| EP | 0250358 | 12/1987 |
| EP | 0258616 | 3/1988 |
| EP | 0290041 | 11/1988 |
| EP | 0290047 | 11/1988 |
| EP | 0292689 | 11/1988 |
| EP | 0292761 | 11/1988 |
| EP | 0304780 | 3/1989 |
| EP | 0331616 | 9/1989 |
| EP | 0347947 | 12/1989 |
| EP | 0169299 | 4/1990 |
| EP | 0374947 | 6/1990 |
| EP | 0405704 | 1/1991 |
| EP | 0454078 | 10/1991 |
| EP | 0455380 | 11/1991 |
| EP | 0463644 | 1/1992 |
| EP | 0485045 | 5/1992 |
| EP | 0535668 | 4/1993 |
| EP | 0543482 | 5/1993 |
| EP | 0661279 | 7/1995 |
| EP | 0279307 | 11/1996 |
| FR | 2354993 | 1/1978 |
| FR | 2643370 | 8/1990 |
| WO | WO 85/02772 | 7/1985 |
| WO | WO 85/05554 | 12/1985 |
| WO | WO 86/01410 | 3/1986 |
| WO | WO 86/02005 | 4/1986 |
| WO | WO 86/02352 | 4/1986 |
| WO | WO 86/02841 | 5/1986 |
| WO | WO 86/06605 | 11/1986 |
| WO | WO 88/07521 | 10/1988 |
| WO | WO 89/01475 | 2/1989 |
| WO | WO 89/01476 | 2/1989 |
| WO | WO 89/12631 | 12/1989 |
| WO | WO 90/03804 | 4/1990 |
| WO | WO 91/03200 | 3/1991 |
| WO | WO 91/18630 | 12/1991 |
| WO | WO 93/03351 | 2/1993 |
| WO | WO 95/15306 | 6/1995 |
| WO | WO 95/28392 | 10/1995 |
| WO | WO 95/32741 | 12/1995 |
| WO | WO 98/05625 | 12/1998 |
| WO | WO 00/38738 | 7/2000 |

OTHER PUBLICATIONS

Best et al., "Chemical and in Vivo Characterization of Gd-bis-Phenylalanyl DTPA Derivatives: A Class of Hepatobiliary MRI Contrast Agents," *Proc. Soc. Magnetic Resonance, Second Meeting*, 1994, 1:264.

Bogdanov et al., "A New Macromolecule as a Contrast Agent for MR Angiography: Preparation, Properties, and Animal Studies," *Radiology*, 1993, 187:701-706.

Brasch et al., "Contrast-Enhanced NMR Imaging: Animal Studies Using Gadolinium-DTPA Complex," 1984, *AJR*, 142:625-630.

Brittain et al., "Luminescence and NMR Studies of the Conformational Isomers of Lanthanide Complexes with an Optically Active Polyaza Polycarboxylic Macrocycle," *Inorg. Chem.*, 1984, 23:4459-4466.

Caravan et al., "Gadolinium (III) Chelates as MRI Contrast Agents: Structure, Dynamics, and Applications," 1999, *Chem. Rev.*, 99:2293-2352.

Carter et al., "Structure of Serum Albumin," *Adv. Protein Chem.*, 1994, 45:153-203.

Chen et al., "Paramagnetic Metalloporphyrins as Potential Contrast Agents in NMR Imaging," *FEBS Letters*, 1984, 168:70-74.

Chu, "The Quantitative Analysis of Structure-Activity Relationships," *Burger's Medicinal Chemistry*, 1980, Part 1, pp. 393-418.

Davison, "Protein Binding," *Fundamentals of Drug Metabolism and Drug Disposition*, 1971, La Du et al. (eds.), pp. 63-75, R.E. Krieger Pub. Co.

Desreux et al., "Nuclear Magnetic Resonance Spectroscopy of Lanthanide Complexes with a Tetraacetic Tetraaza Macrocycle. Unusual Conformation Properties," *Inorg. Chem.*, 1980, 19:1319-1324.

Felix et al., "Brain Tumors: MR Imaging with Gadolinium-DTPA," *Radiology*, 1985, 156:681-688.

Goldstein, "The Interactions of Drugs and Plasma Proteins," *Pharm. Rev.*, 1949, 1:102-165.

Graf et al., "Iron-catalyzed Hydroxyl Radical Formation," *J. Biol. Chem.*, 1984, 259:3620-3624.

Haddock et al., "Biliary Excretion of 668 Chelated Iron," *Proc. Soc. Exptl. Biol. Med.*, 1965, 120:663-668.

Harrison et al., "Hepato-biliary and Renal Excretion in Mice of Charged and Neutral Gadolinium Carboxylic of Cyclic Tetra-azaphosphinic and Complexes Acids", *Magn. Res. Imaging*, 1993, 11:761-770.

He et al., "Atomic Structure and Chemistry of Human Serum Albumin," *Nature*, 1992, 358:209-215.

Hoey et al., "Chemistry of X-Ray Contrast Media," *Radiocontrast Agents*, 1984, Sovak (ed.), Springer-Verlag, pp. 23-125.

Koch-Weser and Sellers, "Binding of Drugs to Serum Albumin (First of Two Parts)," *Medical Intelligence*, 1976, 294(6):311-316.

Koch-Weser and Sellers, "Binding of Drugs to Serum Albumin (Second of Two Parts)," *Medical Intelligence*, 1976, 249(10):526-531.

Konishiroku Photo Industry Co., Ltd., "Processing of Silver Halide Color Photographic Material," *Chemical Abstracts*, 1984, 101:537, Abstract No., 219677p.

Kragh-Hansen, "Molecular Aspects of Ligand Binding to Serum Albumin," *Pharm. Rev.*, 1981, 33(1): 17-53.

Krishnamurthy et al., "Technetium-99m-Iminodiacetic Organic Anions: Review of Biokinetics and Clinical Application in Hepatology," *Hepatology*, 1989, 9:139-153.

Lauffer et al., "Albumin Binding of Paramagnetic Hepatobiliary Contrast Agents: Enhancement of Outer Sphere Relativity", *Nucl. Med. Biol.*, 1988, 15:45-46.

Lauffer et al., "Hepatobiliary MR Contrast Agents: 5-Substituted Iron-EHPG Derivatives," *Magn. Res. Med.*, 1987, 4:582-590

Lauffer et al., "Paramagnetic Metal Complexes as Water Proton Relaxation Agents for NMR Imaging: Theory and Design," *Chem. Rev.*, 1987, 87:901-927.

Lauffer et al., "Preparation and Water Relaxation Properties of Proteins Labeled with Paramagnetic Metal Chelates," *Magn. Res. Imaging*, 1985, 3:11-16.

Lauffer et al., "Stereospecific Binding of rac-Iron (III) N,N' Ethylenebis[(5-bromo-2-hydroxyphenyl)glycinate] to the Bilirubin Site on Human Serum Albumin," *J.A.C.S.*, 1987,109:2216-2218.

Lazar et al., "NMR and Potentiometric Studies of 1,4,7-triazacyclononane-N,N',N"-tris(methylenephosphonate monethylester) and its Complexes with Metal Ions," *Inorganica Chimica Acta*, 1992, 195:89-93.

Lazar et al., "Synthesis and Complexation Properties of a New Macrocyclic Polyaza Polyphosphinate Ligand, DOTEP (1,4,7,10-

Tetraazacyclododecane-1,4,7,10-tetrakis (methyleneethylphosphinate))," *Inorg. Chem.*, 1991, 30:5016-19.

Leo et al., "Partition Coefficients and Their Uses," *Chem. Rev.*, 1971, 71:525-616.

Levi et al., "Two Hepatic Cytoplasmic Protein Fractions, Y and Z, and Their Possible Role in the Hepatic Uptake of Bilirubin, Sulfobromophthalein, and Other Anions," *J. Clin. Invest.*, 1969, 48:2156-2167.

Martell et al., "Development of Iron Chelators for Cooley's Anemia," *Inorganica Chimica Acta*, 1987, 138:215-230.

Martell, "The Design and Synthesis of Chelating Agents", *Development of Iron Chelators for Clinical Use*, 1981, Elsevier North Holland, Inc., pp. 65-104.

McCandlish et al., "Comparison of the Structures and Aqueous Solutions of [o-Phenylelenediaminetetraaceto (4-)] cobalt (III) and [Ethylenedediaminetetraacetato (4-)] cobalt (III) Ions," *Inorg. Chem.*, 1978, 17:1383-1394.

McMurry et al., "The Effect of a Phosphodiester Linking Group on Albumin Binding, Blood Half-Life, and Relaxivity of Intravascular Diethylenetriaminepentaacetato Aquo Gadolinium(III) MRI Contrast Agents," *J. Med. Chem.*, 2002, 45:3465-3474.

Moerlein et al., "The Chemistry of Gallium and Indium as Related to Radiopharmaceutical Production," *Int. J. Nucl. Med. Biol.*, 1981, 8:277-287.

Motekaitis et al., "New Synthetic, Selective, High-Affinity Ligands for Effective Trivalent Metal Ion Binding and Transport," *Inorganica Chimica Acta*, 1982, 198-200:421-428.

Oksendal et al., Biodistribution and Toxicity of MR Imaging Contrast Media, *Magn. Res. Imaging*, 1993, 3:157-165.

Pecoraro et al., "Gallium and Indium Imaging Agents. 2. Complexes of Sulfonated Catechoylamide Sequestering Agents," *Inorg. Chem.*, 1982, 21:2209-2215.

Pratt and Taylor (eds.), "The Binding of Drugs to Plasma Proteins," *Principles of Drug Action. The Basis of Pharmacology*, 1990, Third Edition, Churchill Livingstone, pp. 231-236.

Rayudu, Radiotracers for Medical Applications, 1983, vol. I, pp. 201.

Rocklage et al., "Manganese (II) N,N'-diacetate 5,5'-Bis(phosphate). Synthesis and Characterization of a Paramagnetic Chelate for Magnetic Resonance Imaging Enhancement," *Inorg. Chem.*, 1989, 28:477-485

Rocklage et al., "Structural and Thermodynamic Characterization of Manganese (II) N,N' Dipyridoxylethylendiamine-N,N'-diacetate. A Novel Manganese (II) Chelate," *Inorg. Chem.*, 1988, 27:3530-3534.

Rocklage, "Contrast Agents," Magnetic Resonance Imaging, Mosby Year Book, pp. 372-437 (1992).

Rowland et al., *Clinical Pharmacokinetics: Concepts and Applications*, 1980, Ch. 6, pp. 65-74, Lea & Febiger.

Smidt et al., "Association of Antisense Oligonucleotides with Lipoproteins Prolongs the Plasma Half-life and Modifies the Tissue Distribution", *Nucl. Acids Res.*, 1991, 19(17):4695-4700.

Sorrentino et al., "From Albumin to the Cytoplasm: the Hepatic Uptake of Organic Anions," *Progress in Liver Disease*, 1990, Popper et al. (eds.), W.B. Saunders Co., pp. 203-224.

Sun et al., "Synthesis of Multidentate Ligands Containing Hydroxypryidyl Donor Groups," *Tetrahedron*, 1991, 47:357-364.

Swanson et al., *Pharmaceuticals in Medical Imaging*, 1990, Swanson et al. (eds.), Macmillan Pub., pp. 279-644.

Swanson, "Enhancement Agents for Ultrasound: Fundamentals", *Pharmaceuticals in Medical Imaging*, 1990, Swanson et al. (eds.), Macmillan Pub., pp. 682-687.

Taliaferro et al., "New Multidentate Ligands. 22. N,N'-Dipyridozylethlyenendiamine-N,N'diacetic Acid: a New Chelating Ligand for Trivalent Metal Ions," *Inorg. Chem.*, 1984, 23:188-192.

Taliaferro et al., "New Multidentate Ligands. XXIV. Disodium-N,N'bis(2-hydroxy-5-sulfobenzyl)ethylenediamine-diacetic acid, a New Chelating Ligand for Trivalent Metal Ions," *Chemical Abstracts*, 1984, 101, pp. 369-70, Abstract No. 44224j.

Taliaferro et al., "New Multidentate Ligands. XXIV. Disodium-N,N'bis(2-hydroxy-5-sulfobenzyl)ethylenediamine-diacetic acid, a New Chelating Ligand for Trivalent Metal Ions," *Inorganica Chimica Acta*, 1984, 85:9-15.

Tayyab et al., "Serum albumin; a universal biocarrier," *Med. Sci. Res.*, 1989, 17:1-4.

Thakur, "Radioactive Compounds of 1990, 1:201 Gallium and Indium," *Radiotracers for Medical Applications*, 1990, 1:201.

Theodorakis et al., "Localization of Technetium 99m-Ethylenediamine-N,N'-bis (β-2-hydroxy-5-bromophenyl) acetic Acid and Technetium 99m-N-(2-Mercapto-1-oxopropyl)glycine in Hepatobiliary System", *J. Pharm. Sci.*, 1980, pp. 581-584.

Tilcock et al., "Polymer-Derivatized Technetium $^{99m}$Tc-labeled Liposomal Blood Pool Agents for Nuclear Medicine Applications," *Biochim. Biophys. Acta*, 1993, 1148:77-84.

Tyler et al., "In Vivo Enhancement of Ultrasonic Image Luminance by Aqueous Solutions with High Speed of Sound", *Ultrasonic Imaging*, 1981, 3:323-329.

Unger et al., "Magnetic Resonance Imaging Using Gadolinium-Labeled Monoclonal Antibody," *Invest. Radiology*, 1985, 20:693-700.

Vallner, "Binding of Drugs by Albumin and Plasma Protein," *J. Pharm. Sci.*, 1977, 66(4):447-465.

Vexler et al., "Gd-bis-Phenylalanyl DTPA Derivatives as Hepatobiliary MRI Contrast Agents: MRI in Normal and Liver Tumor-bearing Rats using $Na_2$[GdDTPA(EtOPhe)$_2$]", *Proc. Soc. Magnet. Res.*, 1994, 2:896.

Villringer et al, "Dynamic Imaging with Lanthanide Chelates in Normal Brain: Contract Due to Magnetic Susceptibility Effects," *Magn. Reson. Med.*, 1988, 6:164-174.

Watson et al., "Contrast Agents," *Magnetic Resonance Imaging*, 1992, Stark et al. (eds.), pp. 372-437.

Weinmann et al., "Characteristics of Gadolinium-DTPA Complex: A Potential NMR Contrast Agent," *AJR*, 1984, pp. 619-624.

White et al., "Derivatives of Gd-DTPA-bis(Phenylalanine) as Hepatobiliary Contrast Agents", *First Meeting of the Society of Magnetic Resonance*, 1994, p. S10.

White et al., "Gadolinium DTPA-bis(Phenylalanine Ethyl Ester) as a Hepatobiliary Contrast Agent: Dependence of Pharmacokinetics Upon Stereochemistry", *Society of Magnetic Resonance in Medicine*, 11th Annual Scientific Meeting, 1992, p. 1438.

Yeh et al., "A New Route to 'Bifunctional' Chelating Agents: Conversion of Amino Acids to Analogs of Ethylenedinitrilo-tetraacetic Acid," *Anal. Biochem.*, 1979, 100:152-159.

Office Action in European Patent Appl. 06 01 6539.6, dated Aug. 31, 2012, 6 pages.

Loberg et al., "Membrane transport of technetium-99M Labeled Radio Pharmaceuticals 1. Brain Uptake by Passive Transport," *J. of Nuclear Medicine*, 1979, 20(11):1181-1188.

Summerville et al., "Evaluation of renal clearance of techneticum-99m PAHIDA in dogs," *J. of Nuclear Medicine*, 1987, 28(5):907-909.

Vanlic-Razumenic et al., "Interaction of $^{99m}$Tc-radiopharmaceuticals with transport proteins in human blood," *Nuclear Medicine and Biology*, 1993, 20(3):363-365.

* cited by examiner

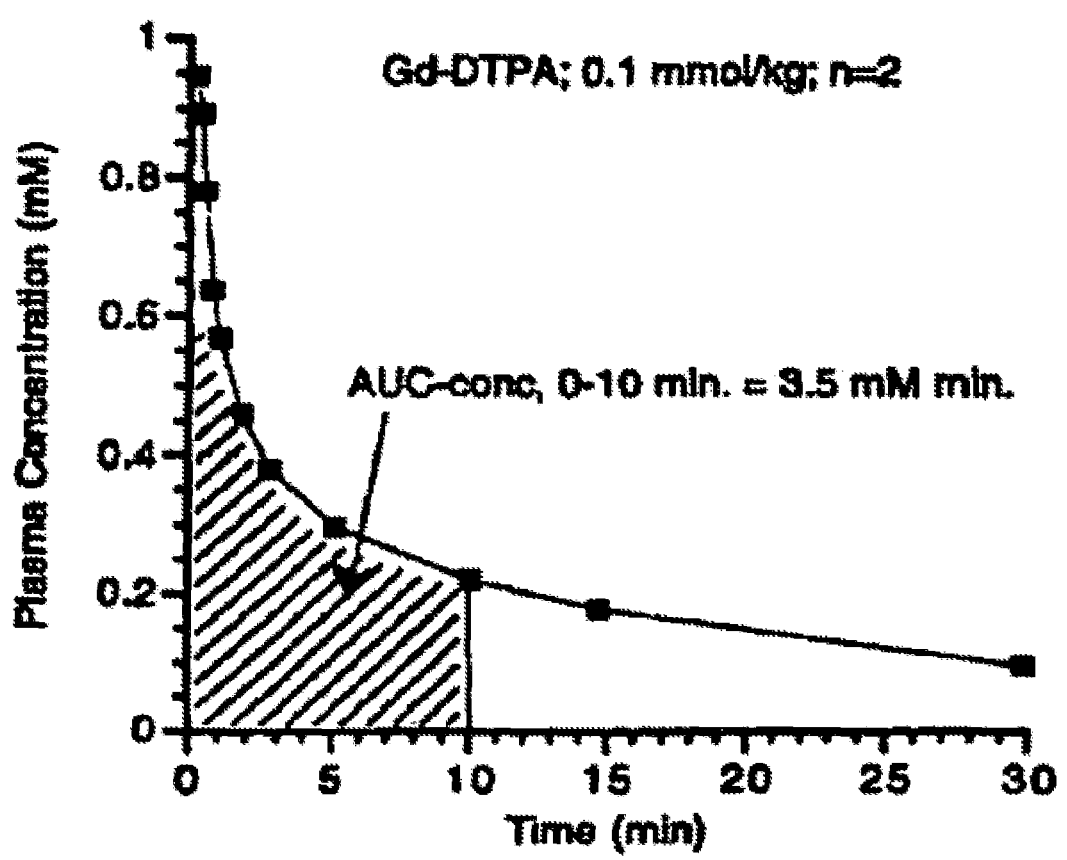

DIAGNOSTIC IMAGING CONTRAST AGENTS WITH EXTENDED BLOOD RETENTION

CROSS-REFERENCES TO RELATED APPLICATIONS

This application is a continuation (and claims the benefit of priority under 35 U.S.C. §120) of U.S. application Ser. No. 11/472,842, filed Jun. 22, 2006, issued as U.S. Pat. No. 8,017, 105, which is a continuation of U.S. application Ser. No. 10/755,507, filed Jan. 12, 2004 now U.S. Pat. No. 7,229,606, which is a continuation of U.S. application Ser. No. 10/034, 522, which issued as U.S. Pat. No. 6,676,929, filed Dec. 20, 2001, which is a continuation of U.S. patent application Ser. No. 08/875,365, filed Dec. 12, 1997 now abandoned, which is a §371 application of International Patent Application No. PCT/US96/00164 (WO 96/23526), filed Jan. 16, 1996, which is a continuation-in-part of U.S. patent application Ser. No. 08/382,317, filed Feb. 1, 1995 now abandoned, all of which are incorporated by reference in their entirety herein. This application is related to U.S. patent application Ser. No. 11/526,302 and U.S. patent application Ser. No. 11/526,312 both filed Sep. 25, 2006, now abandoned. This application is also related to U.S. patent application Ser. No. 10/354,723, filed on Jan. 30, 2003, issued as U.S. Pat. No. 7,011,815, and U.S. patent application Ser. No. 10/755,506, filed Jan. 12, 2004, issued as U.S. Pat. No. 7,060,250.

TECHNICAL FIELD OF THE INVENTION

This invention relates to contrast agents for diagnostic imaging. In particular, this invention relates to novel compounds which exhibit improved blood retention. The compounds comprise:
a) an image-enhancing (or signal-generating) moiety (IEM);
b) a plasma protein binding moiety (PPBM); and
c) a blood half-life extending moiety (BHEM).
This invention also relates to pharmaceutical compositions comprising these compounds and to methods of using the compounds and compositions for blood half-life extension and contrast enhancement of diagnostic

BACKGROUND OF THE INVENTION

Diagnostic imaging techniques, such as magnetic resonance imaging; (MRI), x-ray, nuclear radiopharmaceutical imaging, ultraviolet/visible/infrared light, and ultrasound, have been used in medical diagnosis for a number of years. In some cases, the use of contrast media to improve the image quality or provide specific information has been ongoing for many years. In other cases, such as imaging with light or ultrasound, the introduction of contrast media is imminent.

The contrast agent must interfere with the wavelength of electromagnetic radiation used in the imaging technique, alter the physical properties of tissue to yield an altered signal, or, as in the case of radiopharmaceuticals, provide the source of radiation itself. Commonly used materials include organic molecules, metal ions, salts or chelates, particles (particularly iron particles), or labeled peptides, proteins, polymers or liposomes. After administration, the agent may non-specifically diffuse throughout body compartments prior to being metabolized and/or excreted; these agents are generally known as non-specific agents. Alternatively, the agent may have a specific affinity for a particular body compartment, cell, organ, or tissue; these agents can be referred to as targeted agents.

For agents which are injected or absorbed into the body and distributed by the blood, it is desirable to have an appropriate blood half-life. While extremely long half-lives (i.e., days or weeks) are unnecessary in clinical imaging situations and possibly dangerous (due to the increased chance for toxicity and metabolic breakdown into more toxic molecules), short half-lives are also not desirable. If the image enhancement lasts for too short of time, it is difficult to acquire a high-quality image of the patient. In addition, rapid clearance of a targeted agent will reduce the amount of the agent available to bind to the target site and thus reduce the "brightness" of the target site on the image.

Increasing the blood half-life of an imaging agent involves interfering with one or more of the following clearance mechanisms:

1) Renal Excretion.

Molecules below 60,000 dalton molecular weight, particularly small molecules, can be removed from the blood by nonspecific glomerular filtration in the kidneys. If the molecules exhibit some degree of binding to plasma proteins or other constituents of blood, only the free fraction will be available for filtration and the rate of renal excretion will be reduced accordingly.

(2) Hepatocellular Uptake.

If a molecule possesses hydrophobic character, some fraction of the complex is taken up by liver cells and excreted into the bile. In general, the greater degree of hydrophobicity a molecule possesses, the greater the hepatocyte uptake rate. Though hydrophobicity also leads to plasma protein binding and a reduction in the apparent free concentration of the molecule, the hepatocellular uptake rate can still be very high (D. Sorrentino et al., *Prog. Liver Disease*, pp. 203-24 (1990)), thus reducing the blood half-life. Reduction in blood half-life may or may not be accompanied by an increase in the total hepatobiliary excretion, i.e., the fraction of the administered dose which eventually appears in the feces. The latter quantity is determined by many factors other than the hepatocellular uptake rate, including the extent of cytosolic protein binding inside the hepatocyte, the affinity for canalicular (hepatocyte-to-bile) transport systems, effects on bile flow and enterohepatic recirculation. Extension of blood half-life must be shown by blood or plasma sampling, not simply by measuring decreases in the total hepatobiliary excretion. Similarly, simply obtaining and measuring significant plasma protein binding of a contemplated contrast agent is not sufficient to show that its blood half-life is longer due to lower renal excretion.

3) Reticuloendothelial (RE) or Other Systems.

Large molecular weight substances, such as liposomes, polymers, proteins, and particles, can be rapidly cleared from the blood by recognition (e.g., opsonization, or coating with proteins prior to cellular uptake) and uptake into cells, particularly the RE cells of the liver (the Kupfer cells), spleen and bone marrow.

Two general strategies have been reported to increase blood half-life for imaging agents. One way is to covalently attach the imaging agent via strong or metabolizable chemical bonds to a large molecular weight polymer, protein, liposome, or particle. For example, gadolinium diethylenetriamine-pentaacetic acid (Gd-DTPA) has been attached to human serum albumin (HSA), poly-L-lysine, or dextran (A. N. Oksendal et al., *J. Magn. Reson. Imaging*, 3, pp. 157-165 (1993); S. M. Rocklage, "Contrast Agents," *Magnetic Resonance Imaging*, Mosby Year Book, pp. 372-437 (1992)). This is done to reduce the rate of glomerular filtration in the kidneys and retain the agent in the blood. However, this can lead to long-term retention of the agent. In addition, the firmly bound imaging agents can potentially release toxic by-products such as free metal ions in the metabolism sites for the macromolecule. Furthermore, large conjugates may be difficult to target to specific sites in the body.

The second strategy has been applied to liposomes, polymers, proteins, and particles which are usually rapidly removed from the circulation by the RE system or by other means. The placement of long hydrophilic polymers, such as polyethyleneglycol (PEG), on the surface of the substance reduces uptake by the RE or other systems (C. Tilcock et al., *Biochimica et Biophysia Acta*, 1148, pp. 77-84 (1993); A. A. Bogdanoy et al., *Radiology*, 187, pp. 701-706 (1993)). It is hypothesized that the large, strongly hydrated polymer groups interfere with the molecular process required for recognition and uptake of the substances. The disadvantages of this strategy include: a) high cost and cumbersome manufacturing processes; b); lack of targetability of the large conjugates; and c) applicability appears to be limited to large molecular weight substances.

A particular challenge is for targeted small molecules which possess some lipophilic character. These can suffer from rapid hepatocellular uptake and blood clearance, possibly reducing the "brightness" at the target site. This is a particular problem where lipophilicity is required to achieve targeting to proteins or other biological targets.

A special case of this problem is the development of small molecule blood pool agents. Current small molecule non-specific agents, such as Gd-DTPA for MRI, have relatively fast clearance from the blood and are thus not optimal for imaging blood vessels (i.e., MR angiography) or for monitoring the blood flow into the heart, brain, tumors, or other organs or lesions. Lipophilic agents that target plasma proteins are known in the art. See U.S. Pat. Nos. 4,880,008 and 5,250,285. While these agents bind to plasma protein, in particular to human serum albumin, they can also be subject to rapid hepatocellular uptake and reduced blood half-life.

There remains a need for contrast agents that are retained by the blood for a prolonged period of time.

SUMMARY OF THE INVENTION

The present invention provides diagnostic imaging contrast agents which exhibit improved blood retention. The novel compounds comprise:
a) an image-enhancing (or signal-generating) moiety (IEM);
b) a plasma protein binding moiety (PPBM); and
c) a blood half-life extending moiety (BHEM).
This invention also relates to pharmaceutical compositions comprising these compounds and to methods of using the compounds and compositions for blood half-life extension and contrast enhancement of diagnostic imaging.

These contrast agents exhibit reduced rates of both renal and hepatocellular uptake and no apparent uptake by the RE system. The agents may be targeted to the blood pool or any other biological component. Since the agent is lost less rapidly from the bloodstream, lower doses can be used at a higher margin of safety. The approach is general to both large and small molecules.

BRIEF DESCRIPTION OF THE DRAWINGS

FIG. 1 shows the average plasma concentrations observed after tail vein injection of 0.1 mm/kg of Gd153-labeled DTPA in two rats.

DETAILED DESCRIPTION OF THE INVENTION

In order that the invention herein described may be more fully understood, the following detailed description is set forth.

The term "specific affinity" or "molecular affinity" as used herein, refers to the capability of the contrast agent to be taken up by, retained by, or bound to a particular biological component to a substantially greater degree than other components. Contrast agents which have this property are said to be "targeted" to the "target" component.

The present invention relates to novel compounds which enhance the contrast in diagnostic imaging. These compounds comprise:
a) an image-enhancing (or signal-generating) moiety (IEM);
b) a plasma protein binding moiety (PPBM); and
c) a blood half-life extending moiety (BHEM).
Diagnostic imaging includes, but is not limited to, MRI, x-ray, nuclear radiopharmaceutical imaging, ultraviolet/visible/infrared light, and ultrasound.

Image Enhancing Moiety ("IEM")

According to the present invention, the first domain, IEM, can be any chemical or substance which is used to provide the signal or contrast in imaging.

The signal enhancing domain can be an organic molecule, metal ion, salt or chelate, particle (particularly iron particle), or labeled peptide, protein, polymer or liposome.

A particularly useful IEM is a physiologically compatible metal chelate compound consisting of one or more cyclic or acyclic organic chelating agents complexed to one or more metal ions with atomic numbers 21-29, 42, 44, or 57-83.

For x-ray imaging, the IEM may consist of iodinated organic molecules or chelates of heavy metal ions of atomic numbers 57 to 83. Examples of suitable compounds are described in M. Sovak, ed., "Radiocontrast Agents," *Springer-Verlag*, pp. 23-125 (1984) and U.S. Pat. No. 4,647,447.

For ultrasound imaging, the IEM consists of gas-filled bubbles such as Albunex, Echovist, or Levovist, or particles or metal chelates where the metal ions have atomic numbers 21-29, 42, 44 or 57-83. Examples of suitable compounds are described in Tyler et al., *Ultrasonic Imaging*, 3, pp. 323-29 (1981) and D. P. Swanson, "Enhancement Agents for Ultrasound: Fundamentals," *Pharmaceuticals in Medical Imaging*, pp. 682-87. (1990).

For nuclear radiopharmaceutical imaging or radiotherapy, the IEM consists of a radioactive molecule. More preferred are chelates of Tc, Re, Co, Cu, Au, Ag, Pb, Bi, In, and Ga. Even more preferred are chelates of Tc-99m. Examples of suitable compounds are described in Rayudu G V S, *Radiotracers for Medical Applications*, I, pp. 201 and D. P. Swanson et al., ed., *Pharmaceuticals in Medical Imaging*, pp. 279-644 (1990).

For ultraviolet/visible/infrared light imaging, the IEM consists of any organic or inorganic dye or any metal chelate.

For MRI, the IEM consists of a metal-ligand complex of a paramagnetic form of a metal ion with atomic numbers 21-29, 42, 44, or 57-83.

In order to effectively enhance NMR imaging, the complex must be capable of enhancing the relaxation rates $1/T_1$ (longitudinal, or spin-lattice) and/or $1/T_2$ (transverse, or spin-spin) of water protons or other imaging or spectroscopic nuclei, including protons, P-31, C-13, Na-23, or F-19 on other biomolecules or injected biomarkers. Relaxivities $R_1$ and $R_2$ are defined as the ability to increase $1/T_1$ or $1/T_2$, respectively, per mM of metal ion; units are $mM^{-1}s^{-1}$. For the most common form of clinical MRI, water proton MRI, relaxivity is optimal where the paramagnetic ion bound to the chelating ligand still has one or more open coordination sites for water exchange (R. B. Lauffer, *Chemical Reviews*, 87, pp. 901-927 (1987)). However, this must be balanced with the stability of the metal chelate (vide infra) which generally decreases with increasing numbers of open coordination sites. More preferably, therefore, the complex contains only one or two open coordination sites.

In addition to increasing the $1/T_1$ or $1/T_2$ of tissue nuclei via dipole-dipole interactions, MRI agents can affect two other magnetic properties and thus be of use clinically:

1) an iron particle or metal chelate of high magnetic susceptibility, particularly chelates of Dy, Gd, or Ho, can alter the MRI signal intensity of tissue by creating microscopic magnetic susceptibility gradients (A. Villringer et al, *Magn. Reson. Med.* 6, pp. 164-174 (1988)). No open coordination sites on a chelate are required for this application.

2) an iron particle or metal chelate can also be used to shift the resonance frequency of water protons or other imaging or spectroscopic nuclei, including protons, P-31, C-13, Na-23, or F-19 on other biomolecules or injected biomarkers. Here, depending on the nucleus and strategy used, zero to three open coordination sites may be employed.

The preferred paramagnetic metal is selected from the group consisting of Gd(III), Fe(III), Mn(II and III), Cr(III), Cu(II), Dy(III), Tb(III), Ho(III), Er(III) and Eu(III). The most preferred is Gd(III).

Although the paramagnetic metal is used in a complexed form, toxic effects may still arise due to the dissociation of the metal ion from the complex. The organic chelating ligand should be physiologically compatible. The molecular size of the chelating ligand should be compatible with the size of the paramagnetic metal. Thus gadolinium (III), which has a crystal ionic radius of 0.938 Å, requires a larger chelating ligand than iron (III), which has a crystal ionic radius of 0.64 Å.

In general, the degree of toxicity of a metal chelate is related to its degree of dissociation in vivo before excretion. Toxicity generally increases with the amount of free metal ion. For complexes in which kinetic stability is low, a high thermodynamic stability (a formation constant of at least $10^{15}$ $M^{-1}$ and more preferably at least $10^{20}$ $M^{-1}$) is desirable to minimize dissociation and its attendant toxicity. For complexes in which kinetic stability is comparatively higher, dissociation can be minimized with a lower formation constant, i.e., $10^{10}$ $M^{-1}$ or higher.

Toxicity is also a function of the number of open coordination sites in the complex. The fewer coordination sites, the less tendency there is, generally, for the chelating agent to release the paramagnetic substance. Preferably, therefore, the complex contains two, one or zero open coordination sites. The presence of more than two open sites in general will unacceptably increase toxicity by release of the metal ion in vivo.

Many suitable chelating ligands for MRI agents are known in the art. These can also be used for metal chelates for other forms of biological imaging. For MRI imaging, the preferred IEMs include:

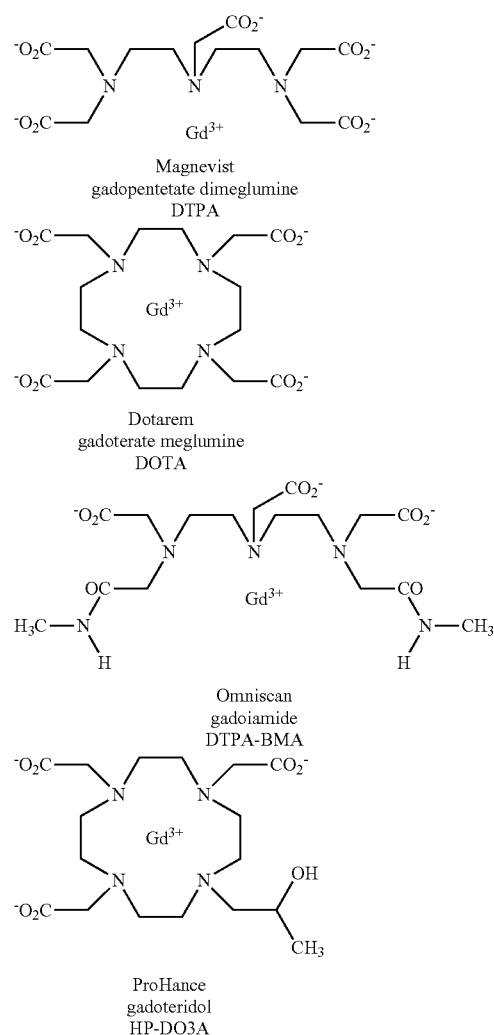

Magnevist
gadopentetate dimeglumine
DTPA

Dotarem
gadoterate meglumine
DOTA

Omniscan
gadoiamide
DTPA-BMA

ProHance
gadoteridol
HP-DO3A

Plasma Protein Binding Moiety ("PPBM")

According to the present invention, the second component of the contrast agents of this invention is a PPBM. This portion of the compound binds the contrast agent to plasma proteins and reduces the rate of renal excretion.

Plasma proteins of interest include albumin, particularly human serum albumin (HSA), which binds molecules possessing some lipophilic portions and either negative charges at physiological pH or partial negatively charged oxygens- or sulphurs or fluorines; alpha acid glycoprotein, which binds primarily positively charged molecules; globulins, which bind steroidal molecules; and lipoproteins, which bind lipophilic or fatty acid-type molecules. The PPBM therefore must be selected properly to achieve the binding to the appropriate protein. Since HSA is present at the highest concentration in serum and has high affinity and capacity for binding a wide range of molecules, it is the preferred plasma protein to be used to increase blood half-lives. HSA is also the preferred plasma protein target because it binds to negatively charged molecules which tend to be less toxic than positively charged molecules.

For binding to HSA, a wide range of hydrophobic or amphiphilic substances may be useful as the PPBM (U. Kragh-Hansen, *Pharm. Rev.*, 33, pp. 17-53 (1981); X. M. He et al., *Nature*, 358, pp. 209-215 (1992); D. C. Carter, *Adv.*

*Protein Chem.,* 45, pp. 153-203 (1994)). These include but are not limited to aliphatic or aryl groups with 1 to 60 carbons as well as any number of nitrogens, oxygens, sulfurs, halogens, alkyl groups, amides, esters, and sulfonamides substituents. Alternatively, the PPBM may be a peptide containing hydrophobic amino acid residues and/or substituents with or without hydrophobic or hydrophilic termination groups. To obtain 10% binding in plasma, the preferred PPBM has at least 7 carbon atoms, more preferably 13, and most preferably 18 carbon atoms.

As stated above, for binding to HSA, a wide range of hydrophobic substances may be useful as the PPBM. In general, binding affinity to HSA and possibly other proteins will increase with the hydrophobicity of the PPBM. Theoretical estimates of the hydrophobicity of a substituent such as a PPBM can be obtained by calculating the contribution to the log of the octanol-water (or octanol-buffer) partition coefficient (log P) for the PPBM itself using the Hansch n constant for substituents. See A. Leo and C. Hansch, "Partition Coefficients and their Uses," *Chemical Reviews,* 71, pp. 525-616 (1971); K. C. Chu, "The Quantitative Analysis of Structure-Activity Relationships," *Burger's Medicinal Chemistry,* Part 1, pp. 393-418, (4th ed. 1980). Binding affinity will increase with increasing log P contributions. For example, for substituents on aliphatic groups, the following n constants can be used:

| Group | n-aliphatic |
|---|---|
| $CH_3$ | 0.50 |
| Phenyl | 2.15 |

For substituents on aryl groups, the following n constants can be used:

| Group | n-aliphatic |
|---|---|
| $CH_3$ | 0.56 |
| $CH_2CH_3$ | 1.02 |
| Phenyl | 1.96 |

Thus, the log P contribution for a p-methylbenzyl group attached to an IEM would be calculated as follows (using the value of the n-aliphatic for $CH_3$ as an estimate for the —$CH_2$— group):

log $P$ contribution=0.50+2.15+0.56=3.21

In binding to HSA, a minimum log P contribution of 2 (equivalent to 4 $CH_3$ groups or one phenyl ring) is required to achieve significant binding. More preferred is a log P contribution of 0.3. Even more preferred is a log P contribution of 4.

HSA binding can be assessed by equilibrium dialysis or ultrafiltration using 4.5% weight/volume HSA in a pH 7.4 buffer. Preferably at least 10%, and more preferably at least 50%, more preferably at least 80%, and most preferably at least 95% of the contrast agent is bound to HSA at a physiological relevant concentrations. (0.01-10 mM in plasma for MRI, x-ray, light, and ultrasound; <1 μM for radiopharmaceuticals). In this application, the measurement of percent binding of the contrast agent to HSA has an error of approximately ±5%. Protein binding to other proteins or to serum can be assessed in a similar fashion.

The addition of lipophilic groups into a contrast agent is likely to decrease the solubility of the agent. To retain efficient solubility of the contrast agent at clinically effective dosage levels or higher, it may be preferred to incorporate one or more hydrogen-bonding groups (oxygen, nitrogens, etc.) into the PPBM.

While purely aliphatic groups can be used as PPBMs, these may not be as preferred as mixed aliphatic-aryl groups or purely aryl groups. Especially when a negative charge is attached to a purely aliphatic groups, particularly long and flexible ones, the contrast agent may interfere with the metabolism of endogenous molecules such as fatty acids or the interactions between membrane proteins and lipids. This may increase the toxicity of the agent. Thus it is preferred that the PPBM contain at least one aryl ring.

In the case of HSA-bound MRI agents for blood pool, tumor, or tissue enhancement, it is especially preferable for the contrast agent to contain two or more distinct lipophilic groups to fully immobilize the agent when bound to the protein. These groups may be on one PPBM, or as two or more separate chemical groups attached to the contrast agent. Because of their bulky nature and rigidity, it is preferable that the two or more groups each consist of an aromatic ring, with the two or more rings in the entire molecule arranged in a rigid, non-planar orientation.

The magnetic efficiency, or relaxivity, of a MRI agent is generally highest when the agent has a rotational correlation time approximately equal to HSA (R. B. Lauffer, *Chemical Reviews,* 87, pp. 901-927 (1987)). While a small molecule such as Gd-DTPA has a rotational correlation time of approximately 0.1 nanoseconds (nsec), HSA has a correlation time of greater than 5-10 nsec; if a chelate has this longer correlation time, the magnetic fluctuations between the paramagnetic ion and the water protons occur on the same time scale as the Larmor frequency, generating the most efficient longitudinal ($T_1$) relaxation possible and thus the highest possible relaxivity. Any flexibility of the chelate when bound to the protein is expected to decrease the effective rotational correlation time and thus decrease relaxivity. Since one site of attachment to the protein may still yield flexibility in several directions, additional sites of attachment may be preferred.

The degree to which an agent has been tuned for maximum relaxivity can be assessed by measuring the relaxivity-bound ($R_1$-bound) in the presence of HSA. This requires measuring the relaxivity of the free chelate ($R_1$-free) as well as the relaxivity ($R_1$-observed) and percent binding of the agent in 4.5% HSA. The $R_1$-observed is a mole fraction weighted average of $R_1$-free and $R_1$-bound:

$R_1$-observed=(fraction-free*$R_1$-free)+(fraction-bound*$R_1$-bound)

Thus:

$$R_1\text{-bound} = \frac{[R_1\text{-observed} - (\text{fraction- free} * R_1\text{-free})]}{\text{fraction- bound}}$$

The benefit of having two or more aryl rings held in a rigid, non-planar fashion can be seen in the following table which shows relaxivity-bound values for MS-322 (56 $mM^{-1}s^{-1}$) and MS-325 (42 $mM^{-1}s^{-1}$) versus MS-317 (34 $mM^{-1}s^{-1}$). The biphenyl or diphenyl groups of MS-322 and MS-325 appear to be restricting the mobility of the HSA-bound contrast agent. In this application, the error associated with the measurement of relaxivity-bound values is approximately ±5%.

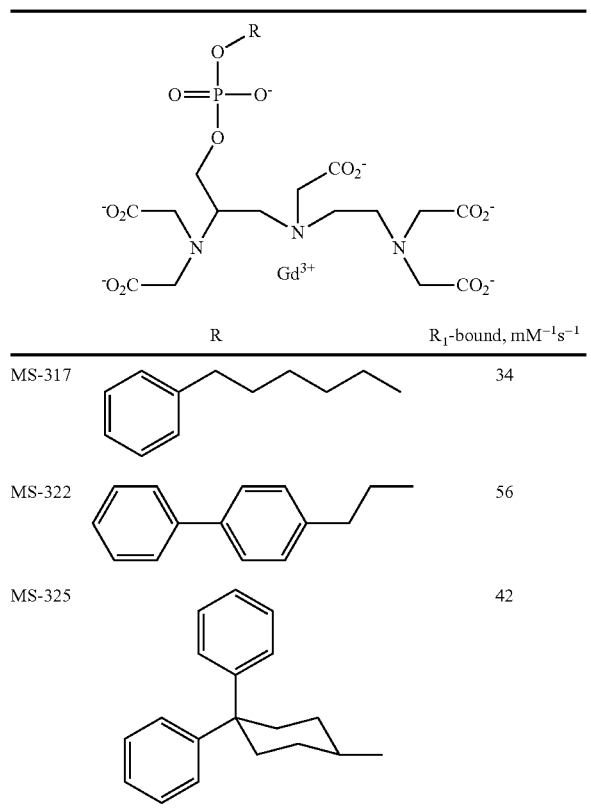

| | R | $R_1$-bound, $mM^{-1}s^{-1}$ |
|---|---|---|
| MS-317 | (phenyl-pentyl) | 34 |
| MS-322 | (biphenyl-ethyl) | 56 |
| MS-325 | (diphenylcyclohexyl) | 42 |

As can be seen in the above table, compounds having two rings rigidly held in a non-planar orientation had higher relaxivity-bound values.

As can be seen in the above equations, the actual $R_1$-observed can be increased by increasing the fraction-bound, that is, increasing the binding affinity of the agent to HSA. This may also lead to lower renal excretion and longer blood half-lives and is thus synergistic. Nevertheless, in order to use the lowest dose and have the highest margin of safety, it is still important to maximize the potency of the agent by maximizing $R_1$-bound.

Blood Half-Life Extending Moiety ("BHEM")

The third domain of the contrast agents of this invention, the BHEM, reduces the rate of hepatocyte uptake of the contrast agent. The balance of hydrophilicity and lipophilicity and the exact molecular structure of a molecule determine its hepatocyte uptake rate.

In the contrast agents of this invention, the BHEMs of this invention reduce or eliminate hepatocyte uptake without unduly interfering with the efficacy of the PPBM. The BHEMs are extremely hydrophilic groups which can hydrogen-bond with water. The presence on a contrast agent of the hydrophilic BHEM reduces the hepatocyte uptake of the agent.

Examples of chemical groups which would serve as a BHEM include carbon, phosphorous, tungsten, molybdenum, or sulfur atoms having attached charged or neutral heteroatoms such as oxygen, nitrogen, sulfur or halogens (especially fluorine) possessing two or more lone electron pairs (i.e., full or partial negative charge) or electropositive hydrogen atoms (i.e., protonated amine) for hydrogen bonding with water. These include groups such as sulfone, ether, urea, thio-urea, amine, sulfonamide, carbamate, peptide, ester, carbonate and acetals. Preferred groups include those which possess one or more partial or full negative charges in aqueous solution at physiological pH wherein the negatively charged atoms cannot be partially or fully neutralized by covalent or coordinate covalent bonding to the IEM. Examples of these preferred BHEMs include negatively charged groups such as phosphate mono-ester, phosphate diester, carboxylate, and sulphonate. More preferred are those which have phosphate groups or any ester forms thereof. Even more preferred are phosphate diesters, since: a) they are highly hydrophilic with four hydrogen-bonding oxygens; b) they are relatively readily synthesized using techniques shown below; c) they serve as excellent linkers between the IEM and the PPBM; and d) because phosphate compounds exist and are metabolized naturally in the body, phosphate diester-containing contrast agents are expected to be non-toxic.

All of the above groups may in turn be attached to a linker moiety linking them to either the IEM, the PPBM, or both. A linker moiety is any physiologically compatible chemical group that does not interfere with the functions of the IEM, PPBM, or BHEM. Preferred linkers are synthetically easy to incorporate into the contrast agent. They are also not so unduly large as to manifest their own undesired biological function or targeting influence onto the contrast agent. Preferably, the length of the linker is between 1 and 50 angstroms, more preferably 1 and 10 angstroms.

The incorporation into a contrast agent of this invention of a BHEM results in prolonged blood retention of the agent. Blood retention is preferably measured by calculating, in a rat plasma pharmacokinetic experiment, the area under the plasma concentration versus time curve ("Area Under the Curve" or "AUC-conc.") for specific length of time (e.g., 0-10 minutes, 0-30 min., 0-60 min., 0-120 min., or 0-infinity). Blood retention (as measured by AUC-conc) can be evaluated experimentally by administration of a contrast agent to rats, rabbits, or higher mammals. It has been observed that blood half-life extension is greater in rabbits and higher mammals than in rats. In this application, blood half-life data, as measured by AUC-conc., represents experimentation in rats. The error associated with this data is approximately ±10%.

The reason that a half-life measurement itself is not used is that the, mathematical definition of this quantity is often not clear and the resulting estimates are variable depending on the pharmacokinetic model used and the length of time the blood samples were obtained.

For example, the average plasma concentrations observed after tail vein injection of 0.1 mmol/kg of $Gd^{153}$-labeled Gd-DTPA in two rats is shown in FIG. 1. Using the Macintosh program KaleidaGraph, this AUC-conc. from 0 to 10 minutes was calculated as 3.5 mM min.

The contrast agents of this invention exhibit an AUC-conc. increase of at least 20% when the BHEM is added to the IEM and PPBM. They preferably exhibit an AUC-conc. increase of at least 40%, more preferably at least 70% and even more preferably at least 100%. In general, the increase in AUC-conc. caused by a BHEM is greater when the binding in plasma is significant, e.g., 20%-50% or greater. The calculated percent increase in AUC-conc. may be different for AUC-conc.'s determined over different time periods. Generally, the percent increase in AUC-conc. caused by the BHEM is greater for AUC-conc.'s taken over longer periods, e.g., 0-30 min., rather than 0-10 min.

Since the structure and physical characteristics of the entire contrast agent molecule will govern its binding in plasma, it is important to select IEMs and BHEMs that are compatible with the desired binding. For example, to achieve binding to the positively charged binding sites on HSA, it is preferred to have IEMs and BHEMs of net neutral or net negative charge to reduce the possibility of repulsion and perhaps even increase binding affinity. For binding to alpha acid glycoprotein, at least some portion of the contrast agent should be positively charged. For binding to globulins, at least some portion of the contrast agent should be steroidal in nature. For binding to lipoproteins, at least some portion of the contrast agent should be lipophilic or fatty acid-like.

The contrast agents of the present invention fall generally into three categories:

1) Blood Pool Agents.

When the binding affinity to plasma proteins is high (i.e., greater than. 50% bound, or preferably greater than 80% bound, or more preferably greater than 95% bound), the agents tend to act primarily as blood pool agents. While the agents can access the interstitial space (the extracellular space in between cells) outside blood capillaries, generally the concentration of relevant plasma proteins such as HSA are lower in that space compared to plasma. Thus, the plasma concentration of the agents is higher than the interstitial concentration, and therefore structures in the body such as blood vessels or tissues containing a large amount of blood vessels are enhanced more than structures with low blood content. The applications for this type of agent include angiography (imaging of blood vessels), perfusion (determining the rate of blood flow into a tissue or tumor using rapid imaging), and blood volume determinations (e.g., to distinguish malignant tumors with good blood supply from benign tumors with lower blood volume).

2) Tissue- or Tumor-Enhancement Agents.

In some cases it is desired to allow the contrast agent to rapidly access the interstitial space and bind to plasma proteins there. For example, in MRI it may be desired to get the greatest possible enhancement from a tissue or tumor as soon as possible after injection. Since protein-bound MRI agents yield greater enhancement than free agents, the best agent would be one which can enter the interstitial space and bind to proteins. However, if the agent is highly bound in plasma, say greater than 95% bound, its transfer rate across the capillaries (determined by the free concentration) is too slow, and very little of the agent gets into the interstitial space and produces signal enhancement of tissue. Likewise, if the binding is only 10%, then the agent is free to enter the interstitial space but has little signal-enhancing power. Thus, a proper balance of transfer rate and binding affinity is required. For these applications, the binding of the agents in plasma should be greater than 10% and less than 95%, or preferably greater than 50% and less than 95%.

This approach is particularly useful in tumor imaging with MRI. Malignant tumors often have better blood flow than benign tumors, and thus rapid imaging of tumor (and interstitial) uptake can often distinguish these tumor types. However, for clinical application, one needs the greatest signal difference between the two tissues to allow clearer discrimination. The signal enhancement via protein binding will help in this regard. In addition, the new, rapidly growing capillaries of malignant tumors are leaky, leading to a higher concentration of plasma proteins in the interstitial space of these tumors. This may lead to greater signal enhancement in the malignant tumors compared to benign tumors with less leaky capillaries.

3) Targeted Agents.

When the agent is targeted to a specific tissue or lesion in the body, a similar logic as that described in the two paragraphs above applies. The relative affinities of the agent for plasma proteins and the target site needs to be balanced such that the agent has some access to bind to the target and at the same time has some binding to plasma proteins to increase blood half-life. For targeted applications, the binding of the agents in plasma should be greater than 10% and less than 95%, or preferably greater than 50% and less than 95%.

The targeting moiety may be a lipophilic substance, receptor ligand, antibody, or other biomolecule that is known to concentrate in the specific biological component desired to be imaged Structural Positioning It is contemplated that the three moieties of the contrast agents of this invention can be arranged in a variety of positions with respect to each other. However, the position of the moieties may not be such that one moiety interferes with the intended function of the other. For example, in an HSA-binding contrasts agent the placement of the BHEM should not block the ability of the PPBM to bind the agent to HSA. Since the major binding sites in HSA are sock-like (X. M. He et al., *Nature*, 3, pp. 209-215 (1992); D. C. Carter, *Adv. Protein Chem.*, 45, pp. 153-203 (1994)), with hydrophobic interiors (especially near the "toe" region) and positively charged "ankle" regions, the binding affinity of a PPBM would decrease if the distal portion of the PPBM were made extremely hydrophilic. As an illustrative example, if the PPBM is a phenyl ring, the most preferred BHEM position on the ring is ortho, followed by meta. A hydrophilic group in the para position would reduce the PPBM's binding affinity to HSA.

For IEMs that consist of a metal chelate, it is preferred that the BHEMs and PPBMs not be attached to the IEM so as to significantly reduce the strength of the binding between the metal ion and chelating ligand. For example, where the chelating arm is acetate, the BHEM or PPBM is preferably not attached to the acetate oxygen.

Another positional requirement is that the BHEM's negatively charged atoms cannot be partially or fully neutralized by covalent or coordinate covalent bonding to the IEM; this ensures that in aqueous systems the very hydrophilic atoms of the BHEM will be highly solvated. For example, when the IEM is a metal chelate, it is important to position the negatively charged atoms of the BHEM so that they cannot become neutralized by the positively charged metal ion ($M^{n+}$) of the IEM through coordinate covalent bonding via th formation of 5- or 6-membered chelate rings the most, stable ring sizes. Since 5-membered chelate rings are the most stable for the metal ions of interest for IEMs (such as gadolinium), it is most important to prevent their formation. Thus, as shown in the drawing below, a phosphinate ($-PO_2-$) or phosphonate ($-PO_3-$) BHEM cannot be attached to the nitrogen atom of an amino carboxylate chelating agent via a $-CH_2-$ linker since this will form a very stable 5-membered chelate ring. Similarly, a phosphodiester ($-OPO_3-$) BHEM should not be attached to the nitrogen atom of an amino carboxylate chelating agent via a $-CH_2-$ linker since this could form a 6-membered chelate ring. However, both of these BHEMs can be attached to other positions, such as the ethylene backbone of the ligand. In some cases, as shown, it may be preferred to increase the length of the linker group to make certain that 5- or 6-membered rings cannot form.

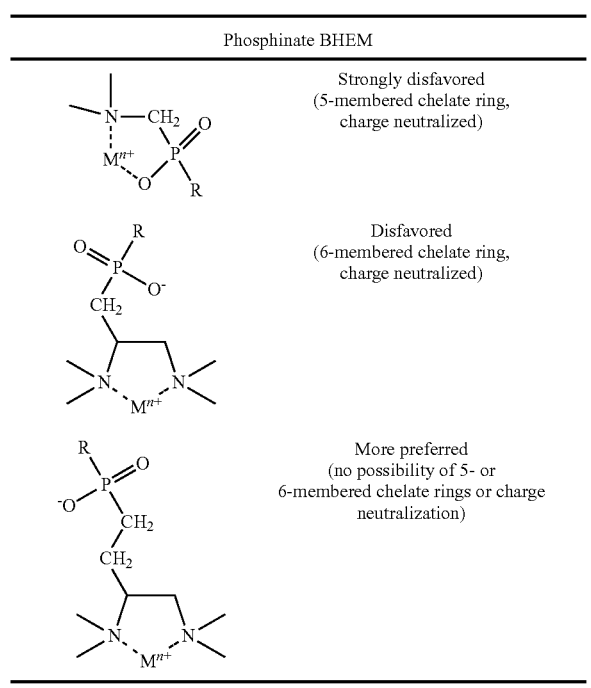

| Phosphinate BHEM | |
|---|---|
| (structure) | Strongly disfavored (5-membered chelate ring, charge neutralized) |
| (structure) | Disfavored (6-membered chelate ring, charge neutralized) |
| (structure) | More preferred (no possibility of 5- or 6-membered chelate rings or charge neutralization) |

It is contemplated that the moieties of this invention can be positioned in the contrast agent so that the following structures may result:

$$IEM-[(L)_m-\{(BHEM)_s-(PPBM)_o\}_p]_q \quad (1)$$

(2)

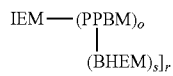
(3)

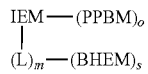

wherein IEM an image-enhancing moiety,
L is a linker moiety,
BHEM is a blood half-life extending moiety,
PPBM is a plasma protein binding moiety,
m can be equal to 0-4,
s, o, and p can be the same or different and equal to 1-4,
and r and q are at least one.

If the moieties of this invention are positioned in the contrast agent as in structure (1) above, the BHEM is preferably sulfone, urea, thio-urea, amine, sulfonamide, carbamate, peptide, ester, carbonate, acetals and more preferably

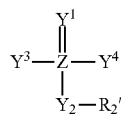

or ester forms,
where
$Z$=P, W, Mo, or S
$Y^1, Y^2$=O or S
$Y^3, Y^4$=O, S or not present
$R_2'$=H, $C_{1-6}$ alkyl or not present.

Most preferably, the BHEM is a phosphate group.

If the moieties of this invention are positioned in the contrast agent as in structure (2) above, the BHEM is preferably sulfone, urea, thio-urea, amine, sulfonamide, carbamate, peptide, ester, carbonate, acetals and more preferably the BHEM has the following formula:

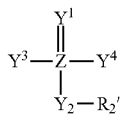

or ester forms,
where
$Z$=P, W, or Mo
$Y^1, Y^2$=O or S
$Y^3, Y^4$=O, S or not present
$R_2'$=H, $C_{1-6}$ alkyl or not present.

Most preferably, the BHEM is a phosphate group.

If the moieties of this invention are positioned in the contrast agent as in structure (3) above, the BHEM is preferably $SO_3^-$ or ester forms, sulfone, urea, thio-urea, amine, sulfonamide, carbamate, peptide, ester, carbonate, acetal and more preferably

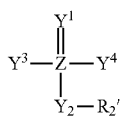

or ester forms,
where
$Z$=P, W, Mo, or S
$Y^1, Y^2$=O or S
$Y^3, Y^4$=O, S or not present
$R_2'$=H, $C_{1-6}$ alkyl or not present.

Most preferably, the BHEM is a phosphate group.

It is contemplated that if the moieties of this invention are positioned in the contrast agent as in structure (3) above, preferred contrast agents have the formulas:

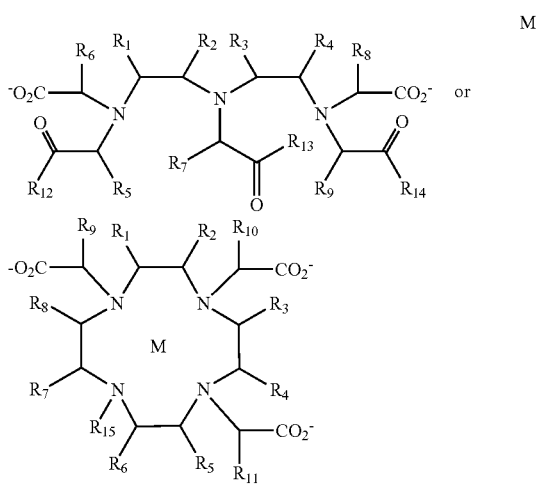

where M is a metal ion with an atomic number of 21-29, 42, 44 or 57-83, where $R_1$, $R_2$, $R_3$, $R_4$, $R_5$, $R_6$, $R_7$, $R_8$, $R_9$, $R_{10}$, $R_{11}$ and $R_{16}$ can be the same or different and selected from the group consisting of H, PPBM, BHEM and $C_{1-6}$ alkyl, provided that at least one of these Rs is PPBM and at least another is BHEM, $R_{12}$, $R_{13}$ and $R_{14}$ can be the same or different and selected from the group consisting of $O^-$ and $N(H)R_{17}$, $R_{15}$=H, $CH_2CH(OH)CH_3$, hydroxy alkyl or $CH(R_{16})COR_{12}$ and $R_{17}$=H or $C_{1-6}$ alkyl.

For contrast agents comprising the formulas shown above, the metal ion M is more preferably Gd(III), Fe(III), Mn(II), Mn(III), Cr(III), Cu(II), Dy(III), Tb(III), Ho(III), Er(III) or Eu(III), and most preferably Gd(III). The BHEM is preferably sulfone, ether, urea, thio-urea, amine, amide, sulfonamide, carbamate, peptide, ester, carbonate, acetal and more preferably $COO^-$ or ester forms, $SO_3^-$ or ester forms and

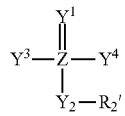

or ester forms, where
Z=P, W, Mo, or S
$Y^1$, $Y^2$=O or S
$Y^3$, $Y^4$=O, S or not present
$R_2'$=H, $C_{1-6}$ alkyl or not present.

In the case of an HSA-binding contrast agent, the BHEM may be placed in between the IEM and the PPBM as shown above in structure (1) or on the IEM away from the PPBM as shown above in structure (3). In this manner the full binding potential of the hydrophobic PPBM group can be expressed without interference from the hydrophilic BHEM group.

The following two pairs of examples serve to show the benefits of a phosphate BHEM inserted in between the IEM Gd-DTPA and two different PPBMs, an octyl $C_8$ aliphatic group and a naphthylmethyl group. Rats were injected intravenously (tail vein) with 0.1 mmol/kg of the $Gd^{153}$ radiolabeled complexes. Plasma concentrations were determined over 30 minutes and fit to a standard bi-exponential two-compartment model. Results for the elimination half-life are shown as well as the area under the plasma concentration versus time curve (AUC-conc.) for the first 10 minutes. In addition, the $1/T_1$s of the plasma samples were recorded (at 20 MHZ, 37° C.) to assess the efficacy as MRI agents. These values were expressed as area under the $1/T_1$ versus time curve (AUC-$1/T_1$) for the first 10 minutes.

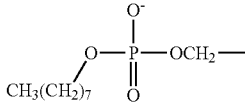

| Cmpd | R | % bound to HSA | $t_{1/2}$, min | AUC-conc mM * min | AUC-$1/T_1$ $s^{-1}$ * min |
|---|---|---|---|---|---|
| DTPA | H | 0 | 15.0 | 3.5 | 27 |
| MS-301 | $CH_3$—$(CH_2)_7$— | 44 | 6.2 | 2.7 | 59 |
| MS-315 | 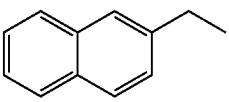 | 56 | 14.0 | 3.4 | 87 |
| MS-310 | 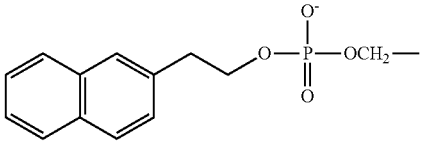 | 30 | 6.8 | 1.8 | 29 |
| MS-321 |  | 40 | 14.0 | 3.2 | 54 |

As shown in the above table, the addition of a phosphate BHEM to MS-301 and MS-310 (resulting in MS-315 and MS-321, respectively) increased the blood half-life of the contrast agent (as measured by AUC-conc.) by 26% and 7.8%, respectively.

The IEM Gd-DTPA is relatively hydrophilic and exhibits little or no binding to HSA. Thus, its relaxivity in plasma is not optimized and its ability to alter the $1/T_1$ (and blood signal on MRI) over time is limited (see the relatively low AUC-$1/T_1$ value). This is despite its relatively long blood half-life of 15 minutes.

To improve the HSA binding and relaxivity, a $C_8$ octyl group can be placed on the 1-position of the DTPA backbone. While this does impart HSA binding to the chelate and some improvement in blood signal, the lipophilic group alone leads to a much-shortened plasma half-life. The insertion of the phosphate-based BHEM actually enhances HSA binding and restores the plasma half-life to a value close to Gd-DTPA. As a result, the blood signal is considerably improved.

The proper placement of the BHEM in these examples shows the importance of this aspect of the invention. The addition of strongly hydrophilic groups to MS-301 or MS-310 enhanced binding to some degree. The placement of the phosphate groups in MS-315 and MS-321 between the IEM and the PPBM may allow the full hydrophobic surface of the PPBMs to interact with the interior of the HSA sites and at the same time create new beneficial interactions (e.g., electrostatic or hydrogen-bonding) between the compound and the "ankle" region of the HSA sites. In particular, it is possible that the negatively-charged phosphate groups are positioned well to interact with the positively-charged residues that line the "ankle" region.

As indicated above, the percentage increase in AUC-conc. can depend on the time for which measurements are made. For example, the addition of the phosphate BHEM onto MS-310 to make MS-321 increased the AUC-conc. for 0-10 min. from 1.8 to 3.2 min., a 78% increase. However, the AUC-conc. for 0-30 min. increased from 2.46 to 5.57 mM min., a 126% increase.

The following contrast agents are made:

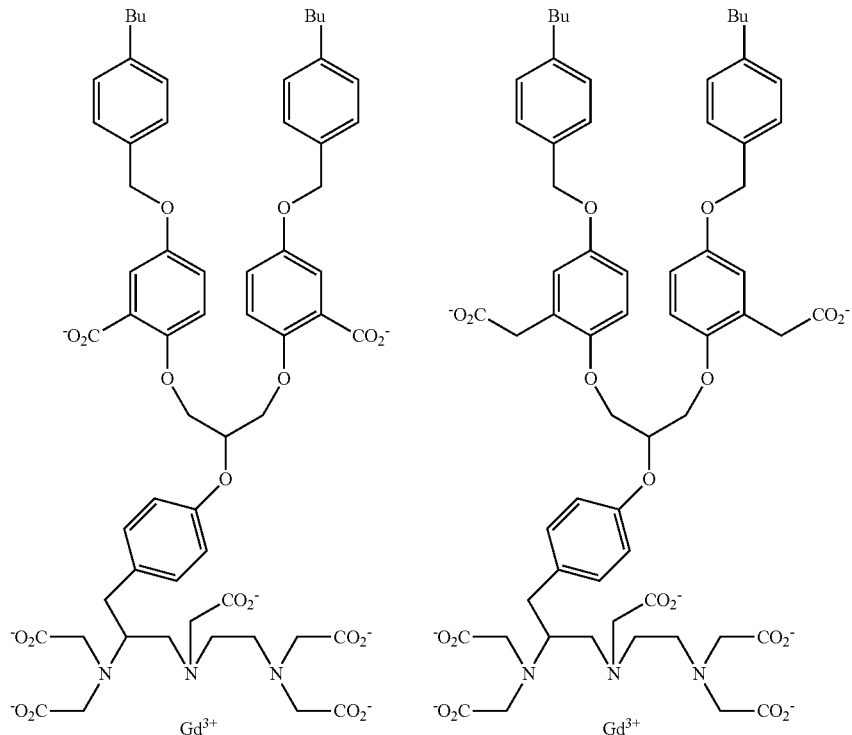

-continued
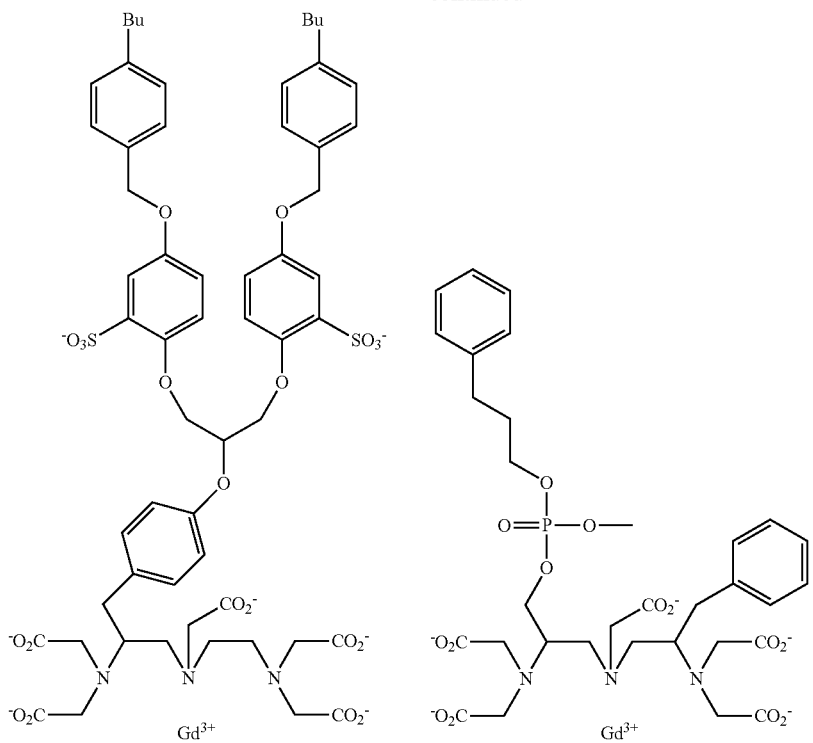
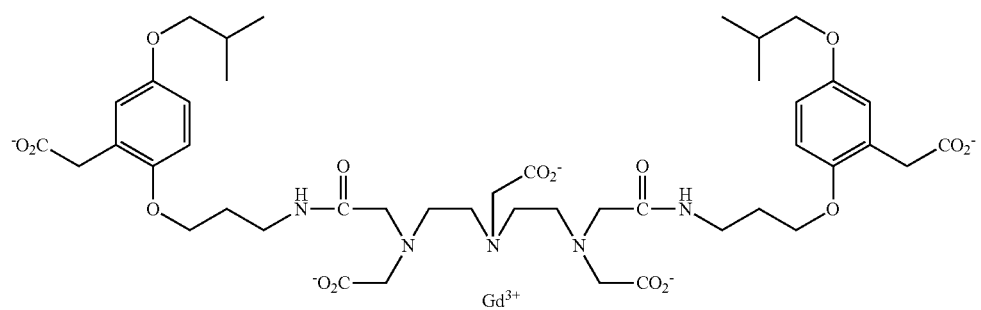
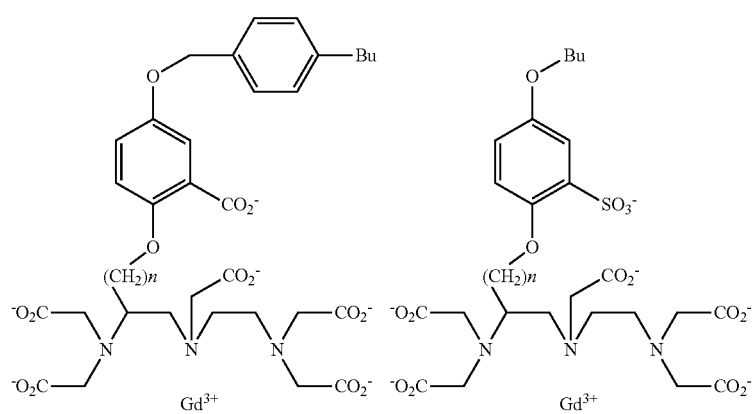

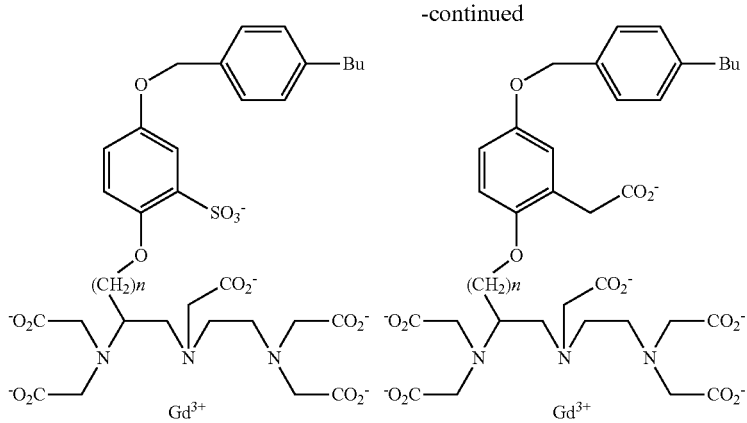
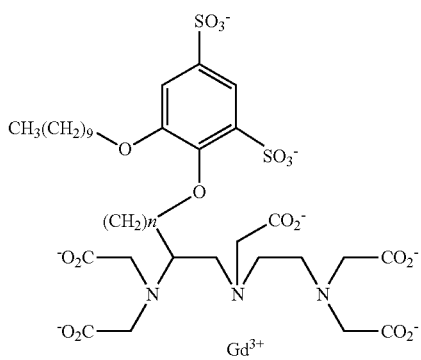
In the above agents, n can be equal to 1-4.
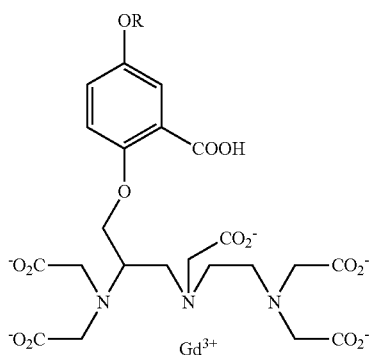
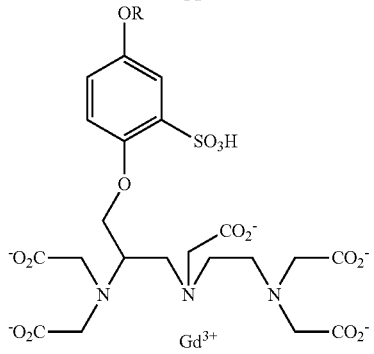
wherein R comprises an aliphatic group and/or at least one aryl ring, or comprises a peptide containing hydrophobic amino acid residues and/or substituents with or without hydrophobic or hydrophilic termination groups.
The preferred contrast agents of this invention are:
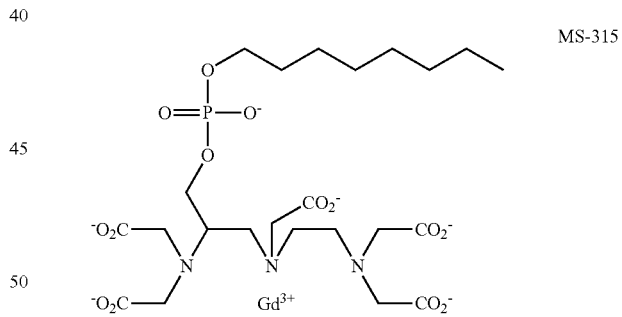
MS-315
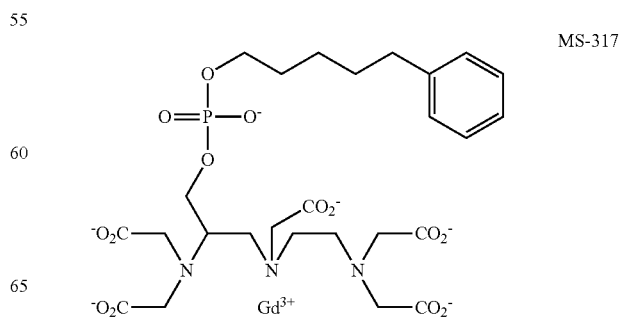
MS-317

MS-322
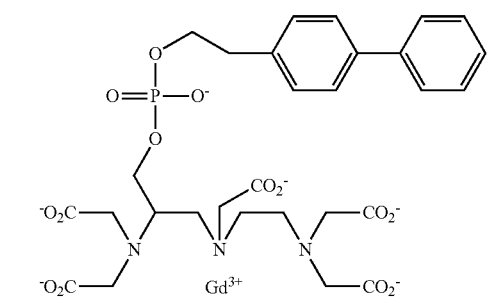

MS-323
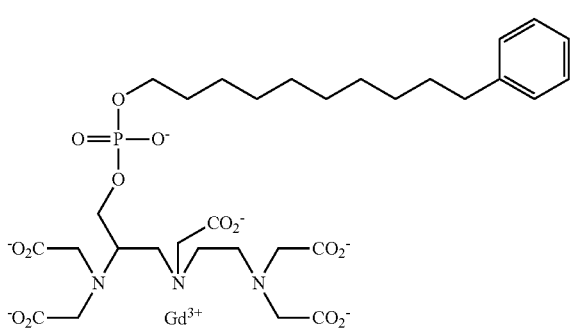

MS-325
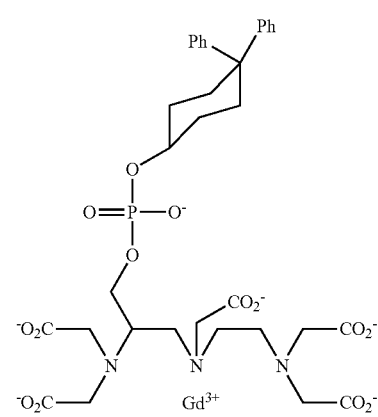

MS-326
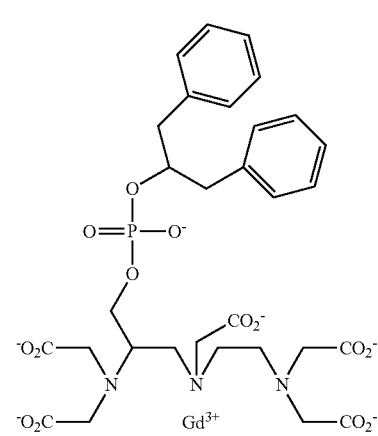

MS-327
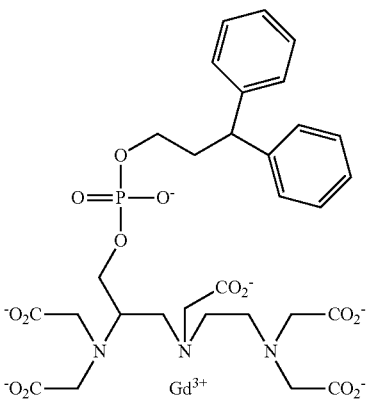

MS-328
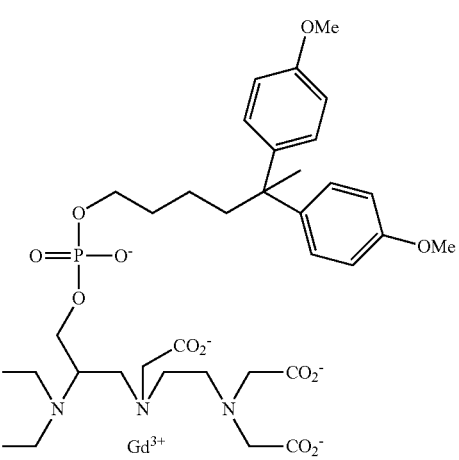

The more preferred contrast agents of this invention are MS-317, MS-322, MS-325 and MS-328. The most preferred is MS-325.

Additional Properties of the Contrast Agents

Since different chiral forms of drugs or biomolecules can influence their performance in vivo, the same is likely to be true of the contrast agents of this invention. For every-given chiral center, one form may have higher relaxivity, blood half-life, lower toxicity, fewer metabolites, or some other advantage or combination of these advantages. These chiral forms will be preferred.

To facilitate administration and uptake, the contrast agents of the present invention should have good water solubility. Preferably, the contrast agents are soluble to a concentration of at least 1.0 mM, and preferably 10 mM, and more preferably 100 mM in water at room temperature.

For injection, the formulated agents should have only moderate viscosity to allow for rapid, convenient injections. The viscosity should be less than 10 centipoise, or preferably less than 5 centipoise, or more preferably less than 2 centipoise.

For injection, the formulated agents should also not have excessive osmolality, since this can increase toxicity. The osmolality should be less than 3000 milliosmoles/kg, or preferably less than 2500 milliosmoles/kg, or most preferably less than 900 milliosmoles/kg.

Use of the Contrast Agents

It is also contemplated that the IEM may comprise a pharmaceutically acceptable salt. Pharmaceutically acceptable salts of this invention include those derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium, magnesium and zinc salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained. The preferred salts of this invention are the N-methyl-D-glucamine, calcium and sodium salts.

The pharmaceutical compositions of this invention comprise any of the complexes of the present invention, or pharmaceutically acceptable salts thereof, together with any pharmaceutically acceptable carrier, adjuvant or vehicle. Pharmaceutically acceptable carriers, adjuvants and vehicles that may be used in the pharmaceutical-compositions of this invention include, but are not limited to, ion exchangers, alumina, aluminum stearate, lecithin, serum proteins, such as human serum albumin, buffer substances such as phosphates, glycine, sorbic acid, potassium sorbate, TRIS (tris(hydroxymethyl)aminomethane), partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Hely or similar alcohol.

Since the contrast agents of this invention bind to plasma proteins, in some cases depending on the dose and rate of injection, the binding sites on plasma proteins may become saturated. This will lead to decreased binding of the agent and could compromise half-life or tolerability. Thus, it may be desirable to inject the agent pre-bound to a sterile albumin or plasma replacement solution. Alternatively, an apparatus/syringe can be used that contains the contrast agent and mixes it with blood drawn up into the syringe; this is then re-injected into the patient.

The compounds and pharmaceutical compositions of the present invention may be administered orally, parenterally, by inhalation spray, topically, rectally, nasally, buccally, vaginally or via an implanted reservoir in dosage formulations containing conventional non-toxic; pharmaceutically-acceptable carriers, adjuvants and vehicles. The term "parenteral" as used herein includes subcutaneous, intravenous, intramuscular, intra-articular, intra-synovial, intrasternal, intrathecal, intrahepatic, intralesional and intracranial injection or infusion techniques.

When administered orally, the pharmaceutical compositions of this invention may be administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, when administered in the form of suppositories for rectal administration, the pharmaceutical compositions of this invention may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

As noted before, the pharmaceutical compositions of this invention may also be administered topically, especially when the target of treatment includes areas or organs readily accessible by topical application, including the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions maybe formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

For administration by nasal aerosol or inhalation, the pharmaceutical compositions of this invention are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Dosage depends on the sensitivity of the diagnostic imaging instrumentation, as well as the composition of the contrast agent. For example, for MRI imaging, a contrast agent containing a highly paramagnetic substance, e.g., gadolinium (III), generally requires a lower dosage than a contrast agent containing a paramagnetic substance with a lower magnetic moment, e.g., iron (III). Preferably, dosage will be in the range of about 0.001 to 1 mmol/kg body weight per day of the active metal-ligand-complex. More preferably, dosage will be in the range of about 0.005 and about 0.05 mmol/kg body weight per day.

It should be understood, however, that a specific dosage regimen for any particular patient will also depend upon a variety of factors, including the age, body weight, general health, sex, diet, time of administration, rate of excretion, drug combination, and the judgment of the treating physician.

If the application of this invention is MRI imaging, following administration of the appropriate dosage of the contrast agent, MRI imaging is carried out. The choice of pulse sequence (inversion recovery, IR; spin echo, SE, echo planar, EPI; time-of-flight, TOF; turbo-flash; gradient echo, GE) and the values of the imaging parameters (echo time, TE; inversion time, TI; repetition time, TR; flip angel, etc.) will be governed by the diagnostic information sought. In general, if one desires to obtain $T_1$-weighted images, then TE should be less than 30 milliseconds (or the minimum value) to maximize $T_1$-weighting. Conversely, if one desires to measure $T_2$, then TE should be greater than 30 milliseconds to minimize competing $T_1$ effects. TI and TR will remain approximately the same for both $T_1$ and $T_2$-weighted images; TI and TR are generally on the order of about 5-1000 and 2-1000 milliseconds, respectively.

The MRI contrast agents of the present invention are useful for general imaging of tumors, blood-brain-barrier breakdown, and other lesions. In addition they are very useful for examining perfusion, i.e., the blood flow into and out of tissues (heart, brain, legs, lungs, kidneys, tumors, etc.), and blood vessels (MR angiography). In addition, the agents can be used to enhance the signal changes in the brain during cognitive events (functional MRI).

It is contemplated that the contrast agents of the present invention may also be used to enhance diagnostic X-ray imaging as well as ultrasound and light imaging. In these cases, the doses of the agent will be approximately equal to that in MRI (0.001-10 mmol/kg). For nuclear imaging, however, the doses will be at tracer levels. For all of these techniques, the use and administration of contrast agents and the settings on the imaging machines is known in the art or uses commonly accepted principles.

In order that this invention may be more fully understood, the following examples are set forth. These examples are for the purpose of illustration only and are not to be construed as limiting the scope of the invention in any way.

EXAMPLES

Experimental

Unless otherwise noted, all materials were obtained from commercial suppliers and used without further purification. THF was distilled from potassium benzophenone ketyl immediately prior to use. Methylene chloride was distilled over calcium hydride. All column chromatography was carried out under nitrogen by flash method described by Still with silica gel (230-400 mesh, EM Separation). All reactions were monitored by thin layer chromatography (TLC) performed on aluminum-backed silica gel 60 $F_{254}$, 0.2-mm plates (EM Separation), and compounds were visualized under UV light (254 nm), Ninhydrin-Plus reagent or Dragendorff's reagent (both Alltech) subsequent heating. Routine proton NMR spectra were recorded at 300 MHZ in $CDCl_3$ with TMS as internal standard, except for the spectra recorded in $D_2O$. Coupling constants (J) are reported in Hertz (Hz). $^{31}P$ NMR spectra were obtained at 121.4 MHZ.

Preparation of Phosphoramidite Intermediate

A. Serine Ethylenediamine Amide

Serine methyl ester hydrochloride (36.03 g, 232 mmol) was dissolved in 400 mL ethylenediamine and was stirred at room temperature for 16 hours. The ethylenediamine was removed by evaporation at reduced pressure. The residue was dissolved in 80 mL 4 N NaOH and was concentrated under reduced pressure. This material was dissolved in methanol (150 mL), filtered and concentrated twice. This residue was suspended in methylene chloride (150 mL) and methanol (5-10 mL) was added with heating until the oily residue was dissolved. The solution was dried over $Na_2SO_4$, filtered through celite and concentrated. The viscous oily product was carried on without further purification.

B. 2-Hydroxymethyldiethylenetriamine Trihydrochloride

The crude amide (<230 mmol) was dissolved in 100 mL THF. Borane.THF (1150 mL, 1.0 M) was added slowly to the stirred solution. The reaction was then refluxed under Ar for 16 hours. The excess borane was quenched by careful addition of 250 mL methanol at 0° C. The reaction mixture was concentrated under reduced pressure. Concentrated HCl (100 mL) was added slowly with cooling and the solution was then refluxed for 24 hours. The product mixture was concentrated under reduced pressure and was crystallized from MeOH/EtOH. This yielded 39.92 g of white solid (71% from methyl ester).

C. 1-Hydroxymethyl-DTPA-penta-t-butyl Ester (1)

To a solution of the hydroxymethyl diethylenetriamine trihydrochloride (30.25 g, 124.70 mmol) and diisopropylethylamine (218 ml, 1.25 mol) in 300 mL of dry DMF at room temperature under $N_2$ was added t-Butyl bromoacetate (126 ml, 0.78 mol) and stirred for 0.24 hours at room temperature. Solvents were then evaporated in vacuo and the residue was dissolved in EtOAc and extracted with $H_2O$, $NaHCO_3$ (sat), $H_2O$ and NaCl (sat). The residue was purified by silica gel column chromatography ($CHCl_3$ only —$CHCl_3$: MeOH=100:1) to give the pure product (oil, 70.12 g, 81.7%): Rf ($CHCl_3$:MeOH=10:1) 0.54, (ether:hexanes=2:1) 0.23; $^1H$-NMR ($CDCl_3$) d 1.44 (brs, 45H), 2.44-3.06 (m, 0.6H), 3.24 and 3.29 (each d, each 1H, J=16.8), 3.34-3.58 (m, 1.0H), 3.66 (dd, 1H, J=11.2, 5.3), 4.20-4.70 (br, 1H).

D. Phosphoramidite Intermediate (2)

To a stirred solution of the penta t-butyl ester (1) (12.88 g, 18.72 mmol) and diisopropylethylamine (4.55 g, 36 mmol) in dist. $CH_2Cl_2$ (100 ml) was added 2-cyanoethyl N,N-diisopropylchloropho-sphoramidite (5.92 g, 0.25 mmol) at room temperature. The mixture was stirred at room temperature for 2 hours, the solution was diluted with 100 mL of $CH_2Cl_2$ and washed with ice-cold 10% $NaHCO_3$ solution (100 ml), $H_2O$ (100 ml), and brine (100 ml) and dried over $MgSO_4$. The organic layer was evaporated to afford crude product as a pale yellow oil (2). This crude oil can be used for the next coupling reaction without further purification.

Examples 1-6 below show the synthesis of some of the preferred contrast agents of this invention according to the following generalized scheme:

Synthesis of Phosphodiester Ligands

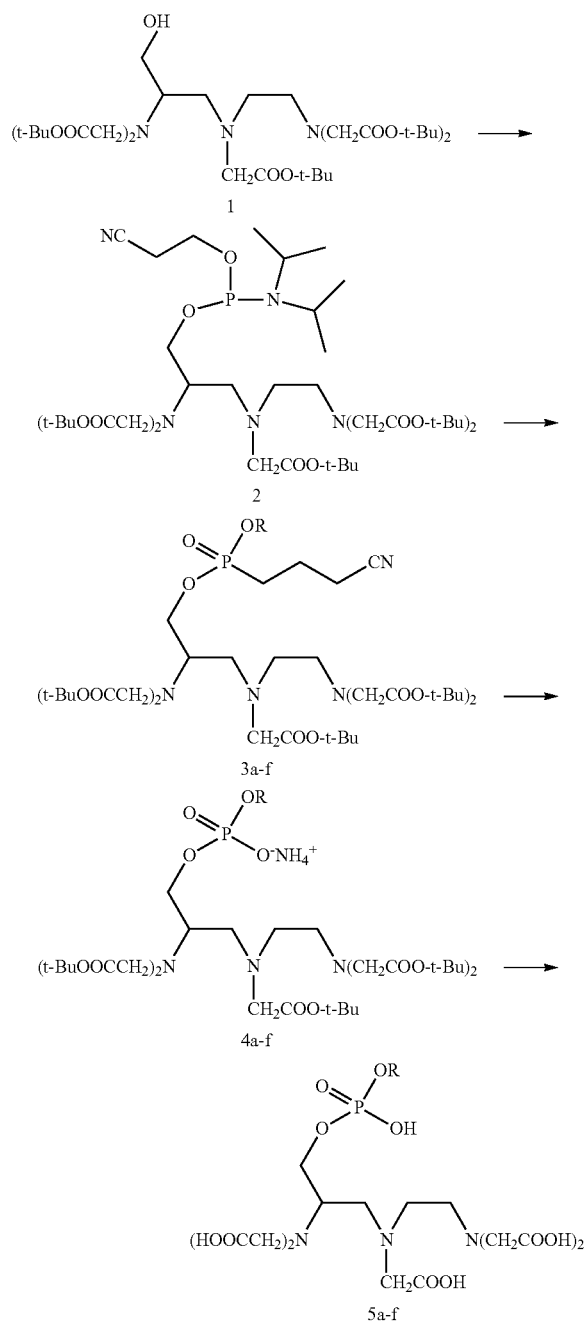

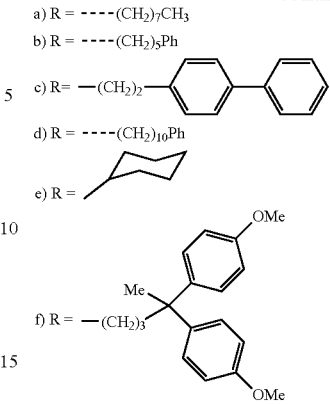

a) R = ----$(CH_2)_7CH_3$
b) R = ----$(CH_2)_5Ph$
c) R= —$(CH_2)_2$—[biphenyl]
d) R = ----$(CH_2)_{10}Ph$
e) R = [cyclohexylmethyl]
f) R = —$(CH_2)_3$—[bis(4-methoxyphenyl)methyl with Me]

Example 1

Preparation of MS-315-(2)-(3a)-(4a)-(5a)

A. n-Octyloxy Phosphate (3a)

Prepared from a crude phosphoramidite intermediate (2) (prepared from 4.40 g, 6.40 mmol of 1-hydroxymethyl-DTPA-penta-t-butyl ester (1)) by the same procedure described for (3d) and purified by silica gel column chromatography ($CHCl_3$/MeOH) [2.71 g, 44.7% total yield from (2)]. $R_f$($CHCl_3$:MeOH=10:1) 0.33.

B. n-Octyl Phosphodiester (4a)

Prepared from the phosphate (3a) (2.70 g, 2.84 mmol) by the same procedure described for (4e) (2.17 g, 85.1%).

C. MS-315 (5a)

The solution of (4a) (2.16 g, 2.41 mmol) in trifluoroacetic acid (20 ml) standing at room temperature for 1 hour. The solvent was evaporated and the residue was dissolved with 5 mL of $H_2O$. The solution was purified with $C_{19}$ reverse phase silica gel column (Sep-Pak pre-packed cartridge, Waters) ($H_2O$ only $CH_3CN$:$H_2O$=1:4) to give the pure product (5a) (1.13 g, 76.2%). $^{31}$P-NMR ($D_2O$) d2.3.

Example 2

Preparation of MS-317-(2)-(3b)-(4b)-(5b)

A. 5-Phenyl-1-pentyloxy Phosphate (3b)

Prepared from a crude phosphoramidite intermediate (2) (prepared from 2.72 g, 3.96 mmol of 1-hydroxy-DTPA-penta-t-butyl ester (1)) by the same procedure described for (3d) except that the crude product (3b) was used for the next reaction without silica gel column chromatography (4.28 g crude). $R_f$($CHCl_3$:MeOH=10:1) 0.26.

B. 5-Phenyl-1-pentyl Phosphodiester (4b)

Prepared from the phosphate (3b) by the same procedure described for (4e) except that the crude product was purified with Sephadex LH 20 chromatography (2.72 g crude). $R_f$($CHCl_3$:MeOH=10:1) 0.11.

C. MS-317 (5b)

Prepared from the crude (4b) (2.72 g) by the same procedure described for (5a) [1.12 g, 43.5% total yield from phosphoramidite intermediate (2)]. $^{31}$P-NMR (D$_2$O) d0.1.

Example 3

Preparation of MS-322-(2)-(3c)-(4c)-(5c)

A. 2-(4-Biphenylyl)-1-ethoxy Phosphate (3c)

Prepared from a purified phosphoramidate intermediate (2) (3.50 g, 3.87 mmol) by the same procedure described for (3d) except that the crude product of (3c) (4.13 g crude) was used for the next reaction without silica gel column chromatography.

B. 2-(4-Biphenylyl)-1-ethyl Phosphodiester (4c)

Prepared from the phosphate (3c) (4.13 g crude) by the same procedure described for (4e) except that the crude product was purified with Sephadex LH 20 chromatography (2.34 g crude).

C. MS-322 (5c)

Prepared from the crude (4c) (2.34 g) by the same procedure described for (5a) [1.15 g, 43.5% total yield from phosphoramidite intermediate (2)]. $^{31}$P-NMR (D$_2$O) d3.7.

Example 4

Preparation of MS-323-(2)-(3d)-(4d)-(5d)

A. 10-Phenyl-1-decanoxy Phosphate (3d)

To a purified phosphoramidiate (2) (15.20 g, 16.81 mmol) in dist. CH$_3$CN (50 ml) was added 10-phenyl-1-decanol (9.00 g, 38.39 mmol) and 1H-tetrazole (2.36 g, 33.70 mmol) in dist CH$_3$CN (50 ml). T-butylhydroperoxide (90%, 2733 ml, 21.00 mmol) was added and reacted and left for 1 hour at room temperature. The solvent was concentrated in vacuo (ca. 10 ml) and the residue was portioned between AcOEt and H$_2$O. The organic layer was washed with H$_2$O and NaCl (sat.), dried, over MgSO$_4$ and evaporated. The residue was purified with silica gel column chromatography (hexanes only—hexanes:ether 1:1 and then CHCl$_3$:MeOH=100:1-50:1) to give the product (3d) (14.12 g, 79.7%). R$_f$ (CHCl$_3$:MeOH=10:1) 0.35.

B. 10-Phenyl-1-decanyl Phosphodiester (4d)

Prepared from the phosphate (3d) (12.27 g, 11.65 mmol) by the same procedure for (4e) (10.52 g, 90.3%). R$_f$ (CHCl$_3$:MeOH=10:1) 0.15.

C. MS-323 (5d)

The mixture of (4d) (10.50 g, 10.50 mmol) in cHCl (trace metal grade, 15 ml) and ether (15 ml) was stirred at room temperature overnight and ether was evaporated in vacuo. To the resulting aqueous layer (pH<0) was added cNaOH to adjust the pH to 1.5. The precipitated white solid was collected by filtration and washed with dil. HCl soln. (pH 1.5, 3 times, 100 mL each) and ether (3 times, 200 mL each). The white solid was dried under pump for 24 hours at room temperature to afford pure product (5d) (6.80 g, 90.0%) $^{31}$P-NMR (D$_2$O+NaOD, PH=13.5) d4.9.

Example 5

Preparation of MS-325-(2)-(3e)-(4e)-(5e)

A. 4,4-Diphenylcyclohexyloxy Phosphate (3e)

Prepared from a purified phosphoramidite intermediate (2) (4.52 g, 5.00 mmol) by the same procedure described for (3d) except that silica gel column chromatography solvents (CH$_2$Cl$_2$ only —CH$_2$Cl$_2$:MeOH 100:1) (2.97 g, 55.4%). R$_f$ (CHCl$_3$:MeOH=10:1) 0.47.

B. 4.4-Diphenylcyclohexyl Phosphodiester (4e)

The solution of (3e) (2.14 g, 2.00 mmol) in 2 M NH$_3$—MeOH (30 ml) was stirred at room temperature for 5 hours. The solvent was evaporated and the residue (4e) (2.00 g, 98.3%) was used for the next reaction without further purification. R$_f$ (CHCl$_3$:MeOH=10:1) 0.12

C. MS-325 (5e)

The mixture of (4b) (2.00 g, 1.96 mmol) in cHCl (trace metal grade, 5 ml) and ether (5 ml) was stirred at room temperature overnight. The solvents were evaporated off and the residue was triturated with H$_2$O (100 ml). The resulting precipitate was filtered and washed with H$_2$O (5 times, 10 mL each) and ether (5 times, 50 mL each). The solid product was dried under pump at room temperature for 24 hours to give the pure product (5b) (1.18 g, 81.5%). $^{31}$P-NMR (D$_2$O+NaOD, pH 13.5) d–0.3.

Example 6

Preparation of MS-328-(2)-(3f)-(4f)-(5f)

A. 4.4-bis(4-Methoxyphenyl)pentyl Phosphate (3f)

Prepared from 32.5 g (36 mmol) of the crude phosphoramidite (2) and 4,4-bis(4-Methoxyphenyl)pentanol (21.06 g, 70 mmol) by the procedure described for (3d). Chromatography was performed in 50% EtOAc/hexane to yield 18.27 g of a yellow oil which was heavily contaminated with the starting alcohol. R$_f$(50% EtOAc/Hex) 0.4.

B. 4,4-bis(4-Methoxyphenyl)pentyl Phosphodiester (4f)

A solution of (30 (18.27 g) was prepared by the same procedure described for (4e) (17.26 g).

C. MS-328 (5f)

Prepared from (4f) (17.26 g) by the procedure described for (5a) yielding 4.88 g of white solid (4.87 mmol, 13% yield from phosphoramidite) $^{31}$P-NMR (D$_2$O) d2.3.

Example 7

In Situ Formulation of the N-methyl-glucamine Salt of the Gadolinium Complex of 5a (MS-315) (200 mM, 5 mL)

Gadolinium oxide (Gd$_2$O$_3$) (0.181 g, 0.5 mmol), compound (5a) (92% by weight, 0.703 g, 1.05 mmol) and N-methyl-glucamine (NMG) (4.1 g, 3.6 mmol) were weighed in a test tube. Deionized water (3.5 mL) was added and the mixture stirred at 95° C. for 7 hours, after which the solution was cooled to room temperature and the volume adjusted to 5.0 mL with deionized water. The solution was filtered through a 2 micron filter to give an aqueous solution of the titled compound.

Example 8

In Situ Formulation of the N-methyl-glucamine Salt of the Gadolinium Complex of 5b (MS-317) (200 mM, 4 mL)

Gadolinium oxide ($Gd_2O_3$) (0.145 g, 0.4 mmol), compound (5b) (81% by weight, 0.706 g, 0.84 mmol) and N-methyl-glucamine (NMG) (0.60 g, 8.1 mmol) were weighed in a test tube. Deionized water (3 mL) was added and the mixture stirred at 95° C. for 6 hours, after which the solution was cooled to room temperature and the volume adjusted to 4.0 mL with deionized water. The solution was filtered through a 2 micron filter to give an aqueous solution of the titled compound.

Example 9

In Situ Formulation of the N-methyl-glucamine Salt of the Gadolinium Complex of 5c (MS-322) (200 mM, 4 mL)

Gadolinium oxide ($Gd_2O_3$) (0.145 g, 0.4 mmol), compound (5c) (79% by weight, 0.729 g, 0.84 mmol) and N-methyl-glucamine (NMG) (0.61 g, 3.1 mmol) were weighed in a test tube. Deionized water (3 mL) was added and the mixture stirred at 95° C. for 6 hours, after which the solution was cooled to room temperature and the volume adjusted to 4.0 mL with deionized water. The solution was filtered through a 2 micron filter to give an aqueous solution of the titled compound.

Example 10

In Situ Formulation of the N-methyl-glucamine Salt of the Gadolinium Complex of 5e (MS-325) (200 mM, 5 mL)

Gadolinium oxide ($Gd_2O_3$) (0.181 g, 0.5 mmol), compound (5e) (95% by weight, 0.820 g, 1.05 mmol) and N-methyl-glucamine (NMG) (0.68 g, 3.5 mmol) were weighed in a test tube. Deionized water (3.5 mL) was added and the mixture stirred at 95° C. for 6 hours, after which the solution was cooled to room temperature and the volume adjusted to 5.0 mL with deionized water. The solution was filtered through a 2 micron filter to give an aqueous solution of the titled compound.

Example 11

In Situ Formulation of the N-methyl-glucamine Salt of the Gadolinium Complex of 5f (MS-328) (200 mM, 5 mL)

Gadolinium oxide ($Gd_2O_3$) (0.181 g, 0.5 mmol), compound (5e) (97% by weight, 0.850 g, 1.05 mmol) and N-methyl-glucamine (NMG) (0.62 g, 3.2 mmol) were weighed in a test tube. Deionized water (3.5 mL) was added and the mixture stirred at 95° C. for 6 hours, after which the solution was cooled to room temperature and the volume adjusted to 5.0 mL with deionized water. The solution was filtered through a 2 micron filter to give an aqueous solution of the titled compound.

Example 12

Preparation of the N-methyl-glucamine Salt of the Gadolinium Complex of 5b (MS-317)

Gadolinium oxide ($Gd_2O_3$) (0.50 g, 1.38 mmol), compound (5b) (87% by weight, 1.87 g, 2.5 mmol) and N-methyl-glucamine (NMG) (1.53 g, 7.8 mmol) were weighed in a test tube. Deionized water (8 mL) was added then the mixture was stirred at 95° C. for 6 hours, after which the solution was cooled to room temperature and the volume adjusted to 9.0 mL with deionized water. The solution was loaded on a 10-g Sep-Pak® column and eluted with water. Solvent was evaporated under reduced pressure, and the solid, white, glassy residue was dried in high vacuo for 48 hours. Yield: 3.50 g (2.48 mmol, 99%). Anal. Calcd. for $(NMGH^+)_3[Gd(5e^{5-})(H_2O] (C_{47}H_{91}GdN_6O_{30}P)$: C, 40.08; H, 6.51; N, 5.97; Gd, 11.16. Found: C, 40.24; H, 6.69; N, 5.88; Gd, 10.11.

Example 13

Preparation of the N-methyl-glucamine Salt of the Gadolinium Complex of 5d (MS-323)

Gadolinium chloride hexahydrate ($GdCl_3.6H_2O$) (2.11 g, 5.68 mmol), compound 5d (74% by weight, 5.82 g, 5.98 mmol) and N-methyl-glucamine (NMG) (6.06 g, 31 mmol) were weighed in a 50-mL round bottom flask. Deionized water (16 mL) was added then the mixture was stirred at 95° C. for 4 hours, and cooled to room temperature. The solution was loaded on a C-18 column (200 g) and eluted with water-methanol 1:1 mixture. Solvent was evaporated under reduced pressure to give a white, glassy solid. Yield: 8.0 g (5.41 mmol, 95%). Anal. Calcd. for $(NMGH^+)_3[Gd\ (5d^{5-})(H_2O] (C_{52}H_{100}GdN_6O_{30}P)$: C, 42.27; H, 6.82; No 5.69; Gd, 10.64. Found: C, 42.04; H, 7.03; N, 5.83; Gd, 9.55.

Example 14

The following contrast agent has a binding to HSA of over 95%.

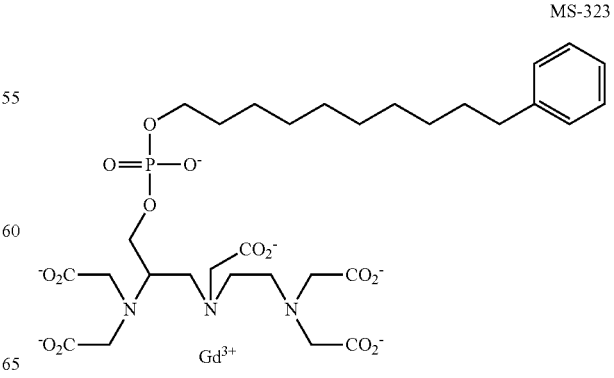

MS-323

It is shown to have an AUC-conc. (for 0 to 10 minutes) 100% or more greater than that of the following analogue:

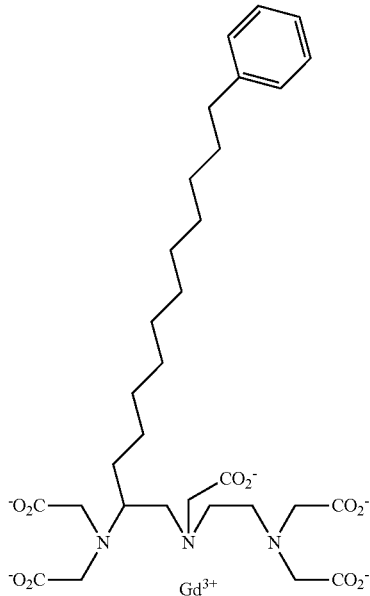

What is claimed is:

1. A method for examining vasculature of a tissue comprising HSA in a human, said method comprising:

a) administering a diagnostic imaging contrast agent, or a pharmaceutically acceptable salt thereof, to said human, said diagnostic imaging contrast agent having the following formula:

IEM-L-BHEM-PPBM or a pharmaceutically acceptable salt thereof, wherein PPBM is a plasma protein binding moiety, wherein the plasma protein is human serum albumin (HSA); wherein the PPBM has 7-18 carbon atoms and comprises at least 1 aryl ring selected from phenyl, naphthyl, biphenyl, and benzyl;

wherein IEM is an image enhancing moiety and is selected from the following group:

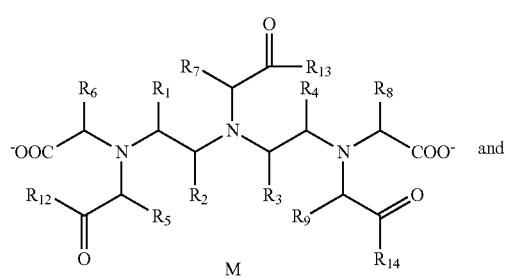

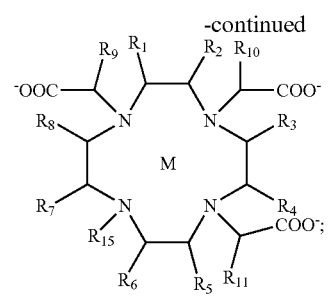

wherein one of $R_1$-$R_{11}$ is L-BHEM-PPBM and the $R_1$-$R_{11}$ groups that are not L-BHEM-PPBM are hydrogen;

wherein $R_{12}$, $R_{13}$, and $R_{14}$ can be the same or different and are selected from the group consisting of $O^-$ and $NH_2$;

wherein $R_{15}$ is H, $CH_2CH(OH)CH_3$, hydroxyl alkyl, or $CH_2COR_{12}$;

wherein said M is a paramagnetic metal ion chelated by the IEM and selected from the group consisting of Gd(III), Fe(III), Mn(II), Mn(III), Cr(III), Cu(II), Dy(III), Tb(III), Ho(III), Er(III), and Eu(III);

wherein L is a linker connecting the IEM to the BHEM consisting of 1 to 4 —$CH_2$— groups; and wherein the BHEM moiety is a blood half-life extending moiety and is a phosphodiester; and b) obtaining an MR image of said tissue.

2. The method of claim 1, wherein the IEM moiety is:

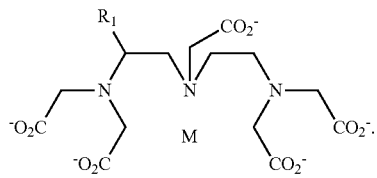

3. The method of claim 1, wherein the IEM is a pharmaceutically acceptable salt, wherein the pharmaceutically acceptable salt is selected from the group consisting of: N-methyl-D-glucamine, calcium, and sodium.

4. The method of claim 1, wherein the pharmaceutically acceptable salt is a trisodium salt.

5. The method of claim 1, wherein said L is a —$CH_2$— group.

6. The method of claim 1, wherein the PPBM binding moiety is selected from the group consisting of:

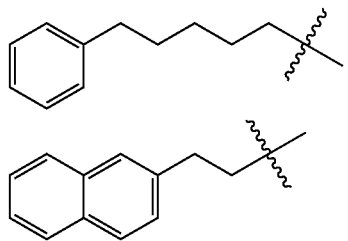

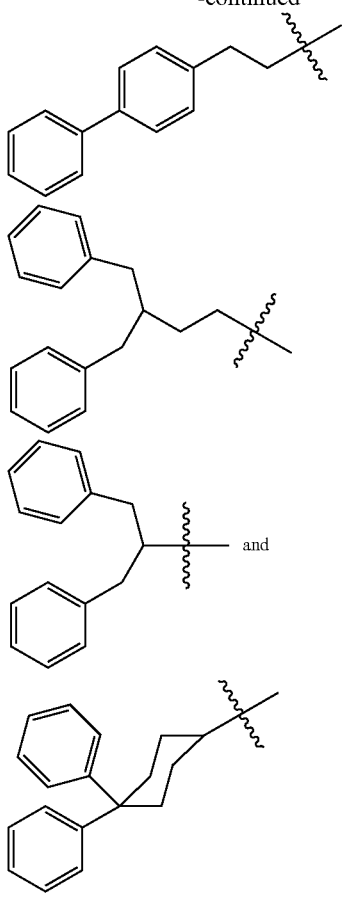

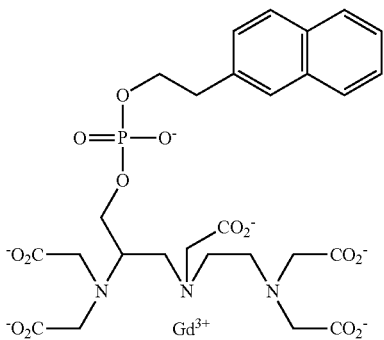

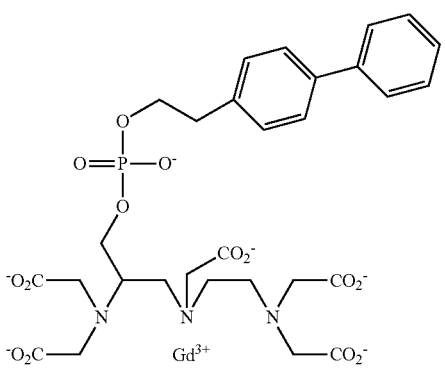

where the wavy line signifies attachment to the BHEM moiety.

7. The method of claim 1, wherein said tissue is selected from the group consisting of a tumor, a heart, a brain, a leg, a lung, and a kidney.

8. The method of claim 1, wherein a portion of said imaging occurs 10 minutes or later after administration of said diagnostic imaging contrast agent.

9. The method of claim 1, wherein said diagnostic imaging contrast agent is administered to said mammal at a concentration between about 0.001 to about 1 mmol/kg body weight.

10. The method of claim 9, wherein said diagnostic imaging contrast agent is administered to said mammal at a concentration between about 0.005 to about 0.05 mmnol/kg body weight.

11. The method of claim 1, wherein said diagnostic imaging contrast agent is selected from the group consisting of:

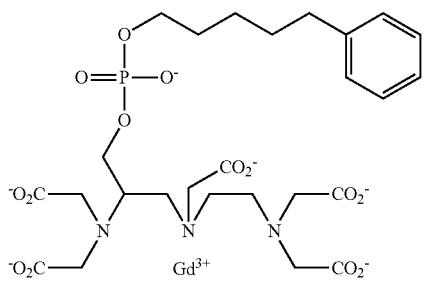

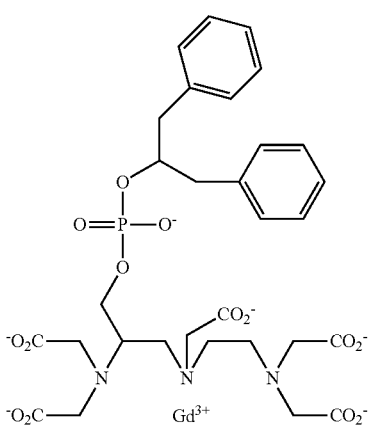

-continued

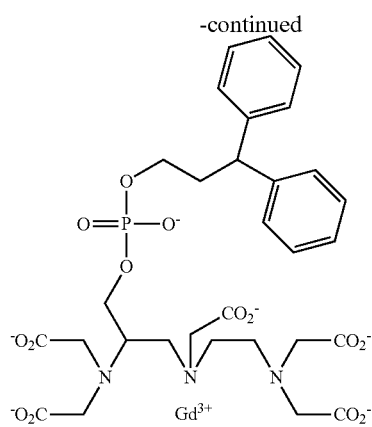

or a pharmaceutically acceptable salt thereof.

12. The method of claim 1, wherein said imaging of said mammal comprises imaging a tumor of said mammal.

13. The method of claim 1, wherein said imaging of said mammal comprises imaging the brain of said mammal.

14. The method of claim 12, wherein said imaging of said brain comprises imaging the blood-brain barrier of said brain.

15. The method of claim 12, wherein said imaging of said brain occurs when said mammal is undergoing cognitive events.

16. A method for examining perfusion in a tissue comprising HSA in a human, said method comprising:
   a) administering a diagnostic imaging contrast agent, or a pharmaceutically acceptable salt thereof, to said human, said diagnostic imaging contrast agent having the following formula:

IEM-L-BHEM-PPBM or a pharmaceutically acceptable salt thereof,
   wherein PPBM is a plasma protein binding moiety, wherein the plasma protein is human serum albumin (HSA); wherein the PPBM has 7-18 carbon atoms and comprises at least 1 aryl ring selected from phenyl, naphthyl, biphenyl, and benzyl;
   wherein IEM is an image enhancing moiety and is selected from the following group:

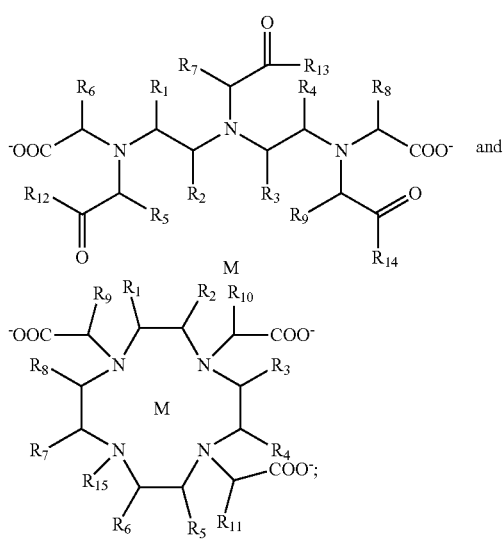

wherein one of $R_1$-$R_{11}$ is L-BHEM-PPBM and the $R_1$-$R_{11}$ groups that are not L-BHEM-PPBM are hydrogen;
wherein $R_{12}$, $R_{13}$, and $R_{14}$ can be the same or different and are selected from the group consisting of $O^-$ and $NH_2$;
wherein $R_{15}$ is H, $CH_2CH(OH)CH_3$, hydroxyl alkyl, or $CH_2COR_{12}$;
wherein said M is a paramagnetic metal ion chelated by the IEM and selected from the group consisting of Gd(III), Fe(III), Mn(II), Mn(III), Cr(III), Cu(II), Dy(III), Tb(III), Ho(III), Er(III), and Eu(III);
wherein L is a linker connecting the IEM to the BHEM consisting of 1 to 4 —$CH_2$— groups; and
wherein the BHEM moiety is a blood half-life extending moiety and is a phosphodiester; and
b) obtaining an MR image of said tissue of said human.

17. The method of claim 16, wherein the IEM moiety is:

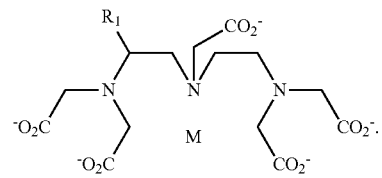

18. The method of claim 16, wherein the IEM is a pharmaceutically acceptable salt, wherein the pharmaceutically acceptable salt is selected from the group consisting of: N-methyl-D-glucamine, calcium, and sodium.

19. The method of claim 18, wherein the salt is a trisodium salt.

20. The method of claim 16, wherein said L is a —$CH_2$— group.

21. The method of claim 16, wherein the PPBM binding moiety is selected from the group consisting of:

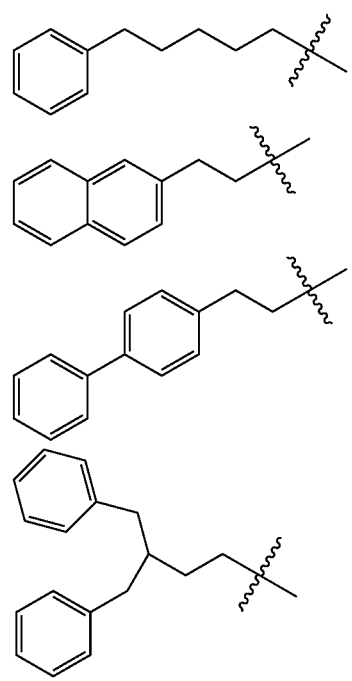

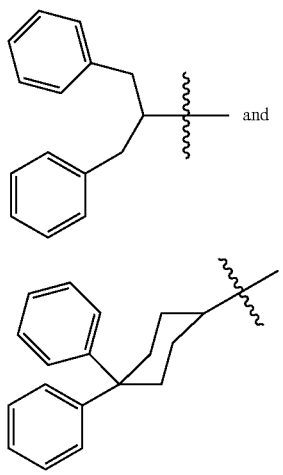

where the wavy line signifies attachment to the BHEM moiety.

22. The method of claim 16, wherein said tissue is selected from the group consisting of a tumor, a heart, a brain, a leg, a lung, and a kidney.

23. The method of claim 16, wherein a portion of said imaging occurs 10 minutes or later after administration of said diagnostic imaging contrast agent.

24. The method of claim 16, wherein said diagnostic imaging contrast agent is administered to said mammal at a concentration between about 0.001 to about 1 mmol/kg body weight.

25. The method of claim 24, wherein said diagnostic imaging contrast agent is administered to said mammal at a concentration between about 0.005 to about 0.05 mmnol/kg body weight.

26. The method of claim 16, wherein said diagnostic imaging contrast agent is selected from the group consisting of:

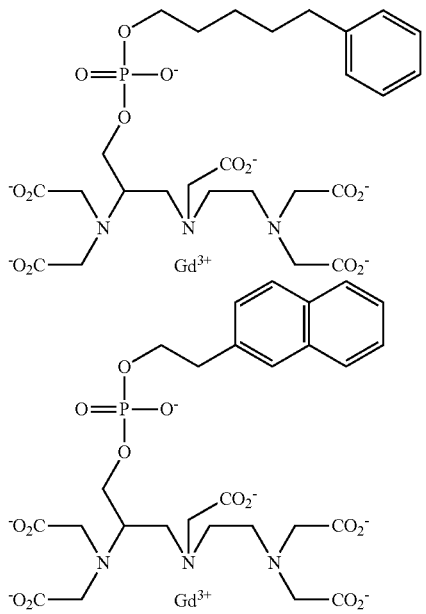

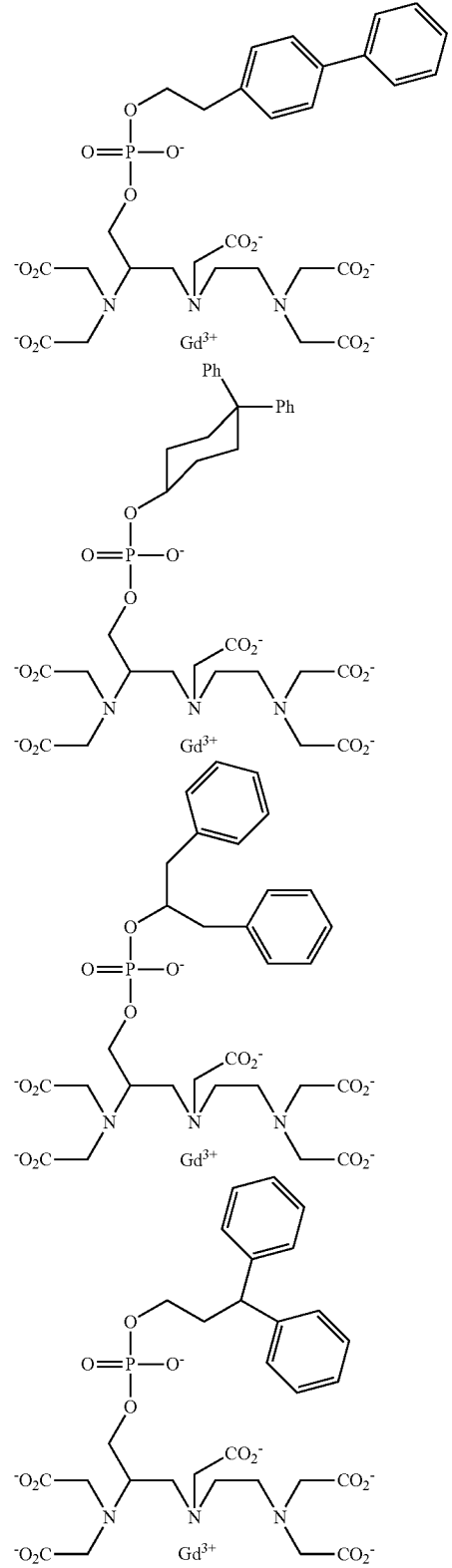

or a pharmaceutically acceptable salt form thereof.

27. The method of claim 16, wherein said imaging of said mammal comprises imaging a tumor of said mammal.

28. The method of claim 16, wherein said imaging of said mammal comprises imaging the brain of said mammal.

29. The method of claim 28, wherein said imaging of said brain comprises imaging the blood-brain barrier of said brain.

30. The method of claim 28, wherein said imaging of said brain occurs when said mammal is undergoing cognitive events.

31. A method of monitoring a human's brain during cognitive events, said method comprising:

a) administering a diagnostic imaging contrast agent, or a pharmaceutically acceptable salt thereof, to said human, said diagnostic imaging contrast agent having the following formula:

IEM-L-BHEM-PPBM or a pharmaceutically acceptable salt thereof, wherein PPBM is a plasma protein binding moiety, wherein the plasma protein is human serum albumin (HSA); wherein the PPBM has 7-18 carbon atoms and comprises at least 1 aryl ring selected from phenyl, naphthyl, biphenyl, and benzyl;

wherein IEM is an image enhancing moiety and is selected from the following group:

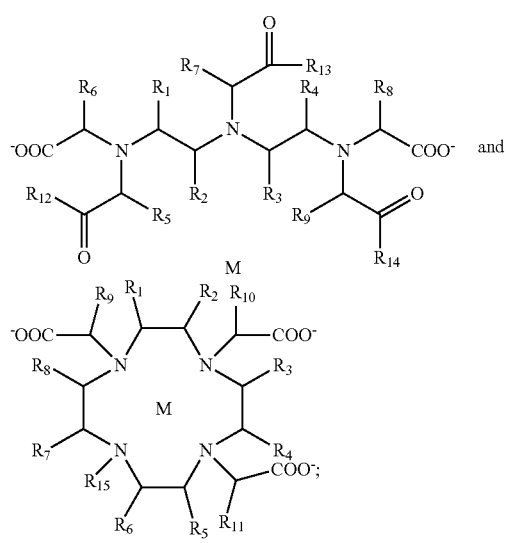

wherein one of $R_1$-$R_{11}$ is L-BHEM-PPBM and the $R_1$-$R_{11}$ groups that are not L-BHEM-PPBM are hydrogen;

wherein $R_{12}$, $R_{13}$, and $R_{14}$ can be the same or different and are selected from the group consisting of $O^-$ and $NH_2$;

wherein $R_{15}$ is H, $CH_2CH(OH)CH_3$, hydroxyl alkyl, or $CH_2COR_{12}$;

wherein said M is a paramagnetic metal ion chelated by the IEM and selected from the group consisting of Gd(III), Fe(III), Mn(II), Mn(III), Cr(III), Cu(II), Dy(III), Tb(III), Ho(III), Er(III), and Eu(III);

wherein L is a linker connecting the IEM to the BHEM consisting of 1 to 4 —$CH_2$— groups; and wherein the BHEM moiety is a blood half-life extending moiety and is a phosphodiester; and b) obtaining an MR image of said brain of said human.

32. The method of claim 31, wherein the IEM moiety is:

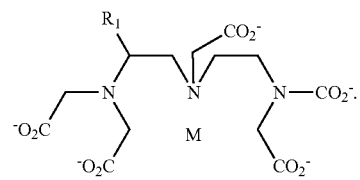

33. The method of claim 31, wherein the IEM is a pharmaceutically acceptable salt, wherein the pharmaceutically acceptable salt is selected from the group consisting of: N-methyl-D-glucamine, calcium, and sodium.

34. The method of claim 33, wherein the pharmaceutically acceptable salt is a trisodium salt.

35. The method of claim 31, wherein said L is a —$CH_2$— group.

36. The method of claim 31, wherein the PPBM binding moiety is selected from the group consisting of:

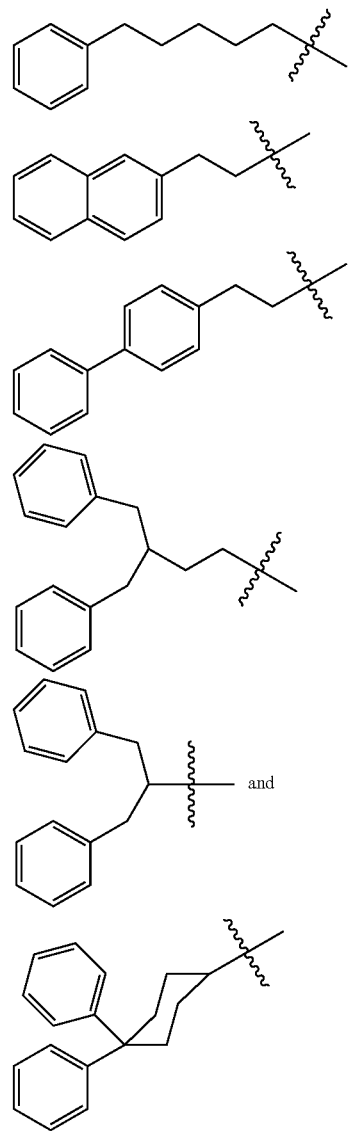

where the wavy line signifies attachment to the BHEM moiety.

37. The method of claim 31, wherein said obtaining occurs during a cognitive event.

38. The method of claim 31, wherein a portion of said imaging occurs 10 minutes or later after administration of said diagnostic imaging contrast agent.

39. The method of claim 31, wherein said diagnostic imaging contrast agent is administered to said mammal at a concentration between about 0.001 to about 1 mmol/kg body weight.

40. The method of claim 39, wherein said diagnostic imaging contrast agent is administered to said mammal at a concentration between about 0.005 to about 0.05 mmnol/kg body weight.

41. The method of claim 31, wherein said diagnostic imaging contrast agent is selected from the group consisting of:

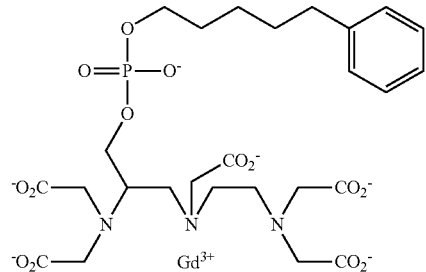

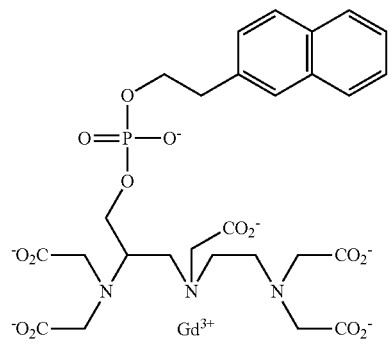

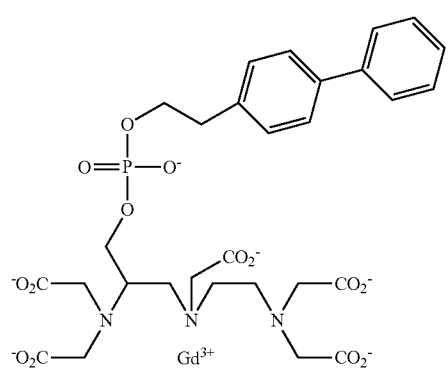

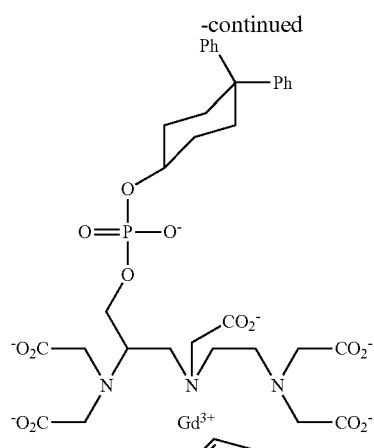

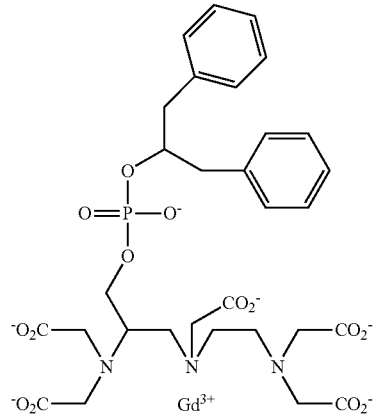

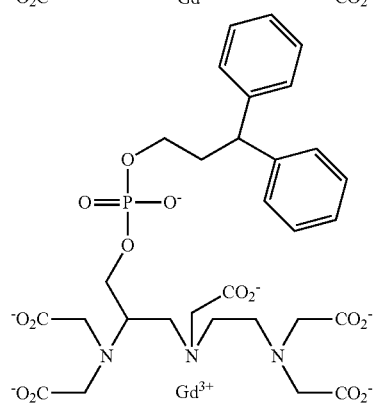

or a pharmaceutically acceptable salt form thereof.

42. A method for determining blood volume in a tissue comprising HSA in a human, said method comprising:
 a) administering a diagnostic imaging contrast agent, or a pharmaceutically acceptable salt thereof, to said human, said diagnostic imaging contrast agent having the following formula:

IEM-L-BHEM-PPBM or a pharmaceutically acceptable salt thereof,
 wherein PPBM is a plasma protein binding moiety, wherein the plasma protein is human serum albumin (HSA); wherein the PPBM has 7-18 carbon atoms and comprises at least 1 aryl ring selected from phenyl, naphthyl, biphenyl, and benzyl;
 wherein IEM is an image enhancing moiety and is selected from the following group:

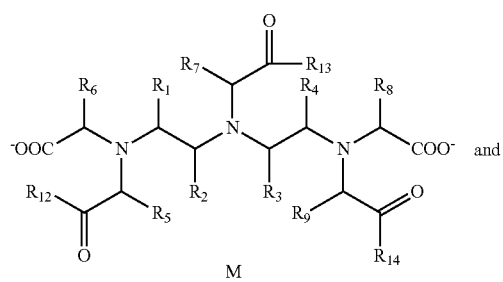

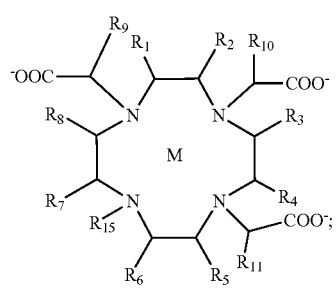

wherein one of $R_1$-$R_{11}$ is L-BHEM-PPBM and the $R_1$-$R_{11}$ groups that are not L-BHEM-PPBM are hydrogen;

wherein $R_{12}$, $R_{13}$, and $R_{14}$ can be the same or different and are selected from the group consisting of $O^-$ and $NH_2$;

wherein $R_{15}$ is H, $CH_2CH(OH)CH_3$, hydroxyl alkyl, or $CH_2COR_{12}$;

wherein said M is a paramagnetic metal ion chelated by the IEM and selected from the group consisting of Gd(III), Fe(III), Mn(II), Mn(III), Cr(III), Cu(II), Dy(III), Tb(III), Ho(III), Er(III), and Eu(III);

wherein L is a linker connecting the IEM to the BHEM consisting of 1 to 4 —$CH_2$— groups; and wherein the BHEM moiety is a blood half-life extending moiety and is a phosphodiester; and b) obtaining an MR image of said brain of said human.

43. The method of claim 42, wherein the IEM moiety is:

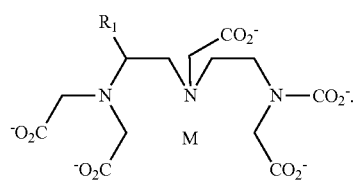

44. The method of claim 42, wherein the IEM is a pharmaceutically acceptable salt, wherein the pharmaceutically acceptable salt is selected from the group consisting of: N-methyl-D-glucamine, calcium, and sodium.

45. The method of claim 44, wherein the pharmaceutically acceptable salt is a trisodium salt.

46. The method of claim 42, wherein said L is a —$CH_2$— group.

47. The method of claim 42, wherein the PPBM binding moiety is selected from the group consisting of:

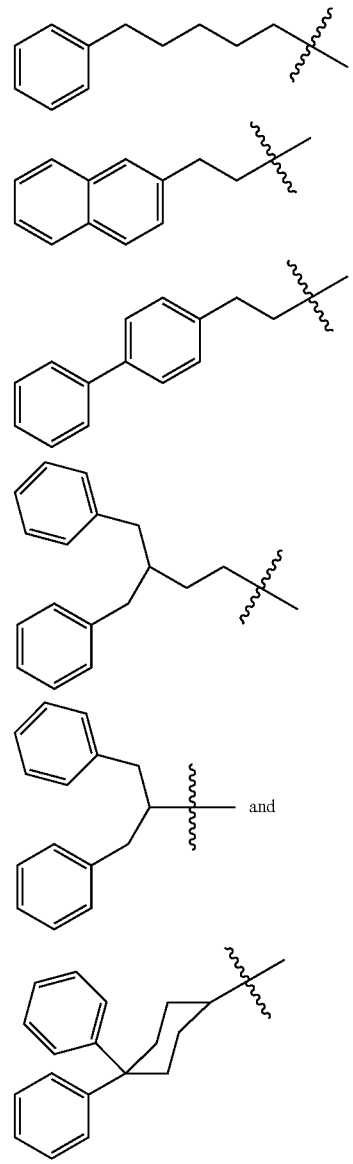

where the wavy line signifies attachment to the BHEM moiety.

48. The method of claim 42, wherein said tissue is selected from the group consisting of a tumor, a heart, a brain, a leg, a lung, and a kidney.

49. The method of claim 42, wherein a portion of said imaging occurs 10 minutes or later after administration of said diagnostic imaging contrast agent.

50. The method of claim 42, wherein said diagnostic imaging contrast agent is administered to said mammal at a concentration between about 0.001 to about 1 mmol/kg body weight.

51. The method of claim 50, wherein said diagnostic imaging contrast agent is administered to said mammal at a concentration between about 0.005 to about 0.05 mmnol/kg body weight.

52. The method of claim 42, wherein said diagnostic imaging contrast agent is selected from the group consisting of:

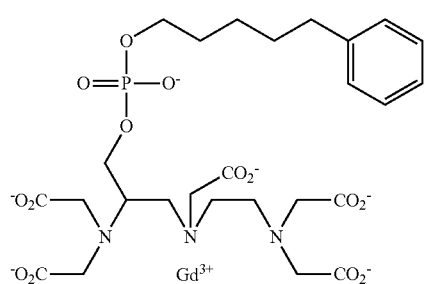

or a pharmaceutically acceptable salt form thereof.

53. The method of claim 42, wherein said imaging of said mammal comprises imaging a tumor of said mammal.

54. The method of claim 42, wherein said imaging of said mammal comprises imaging the brain of said mammal.

55. The method of claim 54, wherein said imaging of said brain comprises imaging the blood-brain barrier of said brain.

56. The method of claim 54, wherein said imaging of said brain occurs when said mammal is undergoing cognitive events.

57. A method of MR imaging of a mammal, said method comprising the steps of:

a) administering to said mammal a diagnostic imaging contrast agent or a pharmaceutically acceptable salt thereof, said diagnostic imaging contrast agent having the formula:

IEM-L-BHEM-PPBM or a pharmaceutically acceptable salt thereof, wherein PPBM is a plasma protein binding moiety, wherein the plasma protein is human serum albumin (HSA); wherein the PPBM has 7-18 carbon atoms and comprises at least 1 aryl ring selected from phenyl, naphthyl, biphenyl, and benzyl;

wherein IEM is an image enhancing moiety and is selected from the following group:

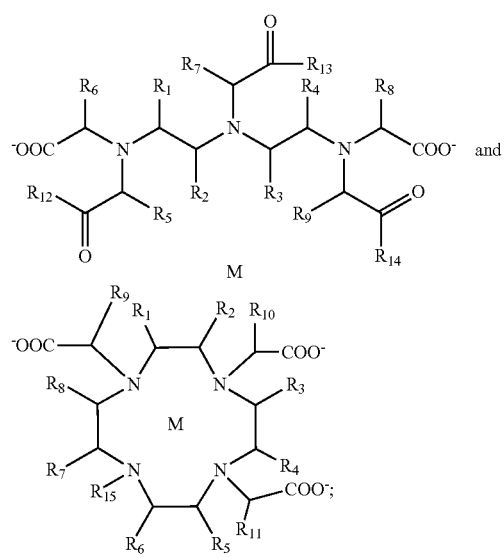

wherein one of $R_1$-$R_{11}$ is L-BHEM-PPBM and the $R_1$-$R_{11}$ groups that are not L-BHEM-PPBM are hydrogen;

wherein $R_{12}$, $R_{13}$, and $R_{14}$ can be the same or different and are selected from the group consisting of $O^-$ and $NH_2$;

wherein $R_{15}$ is H, $CH_2CH(OH)CH_3$, hydroxyl alkyl, or $CH_2COR_{12}$;

wherein said M is a paramagnetic metal ion chelated by the IEM and selected from the group consisting of Gd(III), Fe(III), Mn(II), Mn(III), Cr(III), Cu(II), Dy(III), Tb(III), Ho(III), Er(III), and Eu(III);

wherein L is a linker connecting the IEM to the BHEM consisting of 1 to 4 —$CH_2$— groups; and wherein the BHEM moiety is a blood half-life extending moiety and is a phosphodiester; and b) subjecting said mammal to MR imaging.

58. The method of claim 57, wherein the IEM moiety is:

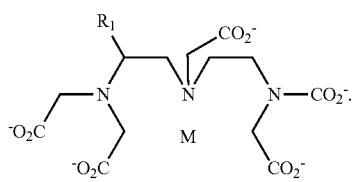

59. The method of claim 57, wherein the IEM is a pharmaceutically acceptable salt, wherein the pharmaceutically acceptable salt is selected from the group consisting of: N-methyl-D-glucamine, calcium, and sodium.

60. The method of claim 57, wherein the pharmaceutically acceptable salt is a trisodium salt.

61. The method of claim 57, wherein said L is a —$CH_2$— group.

62. The method of claim 57, wherein the PPBM binding moiety is selected from the group consisting of:

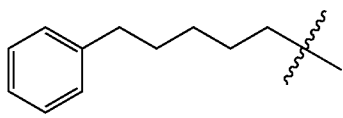

-continued

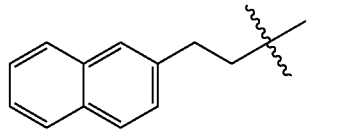

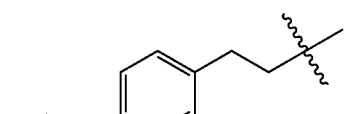

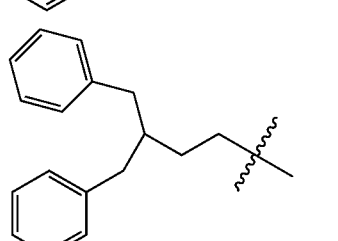

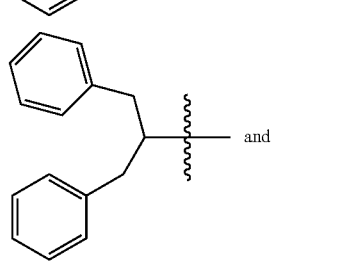 and

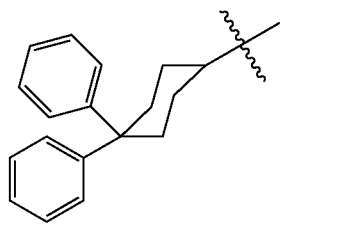

where the wavy line signifies attachment to the BHEM moiety.

63. The method according to claim 57, wherein said mammal is a human.

64. The method according to claim 57, wherein said MR imaging comprises imaging at least a portion of the vasculature of said mammal.

65. The method according to claim 57, wherein a portion of said imaging occurs 10 minutes or later after administration of said diagnostic imaging contrast agent.

66. The method according to claim 57, wherein said diagnostic imaging contrast agent is administered to said mammal at a concentration between about 0.001 to about 1 mmol/kg body weight.

67. The method according to claim 66, wherein said diagnostic imaging contrast agent is administered to said mammal at a concentration between about 0.005 to about 0.05 mmnol/kg body weight.

68. The method according to claim 57, wherein said diagnostic imaging contrast agent is selected from the group consisting of:

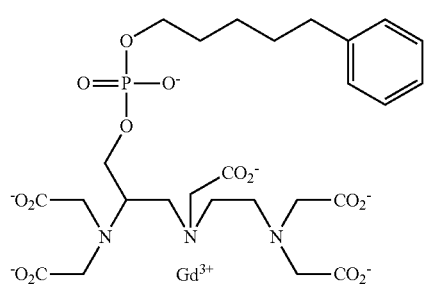

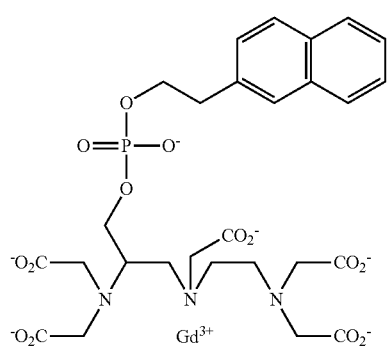

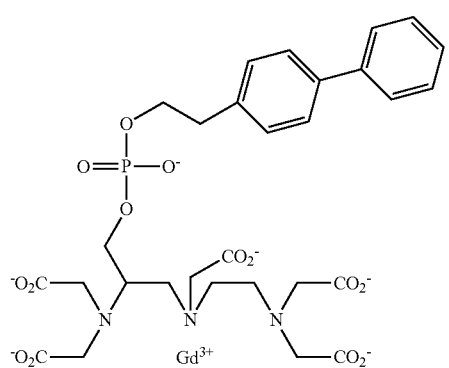

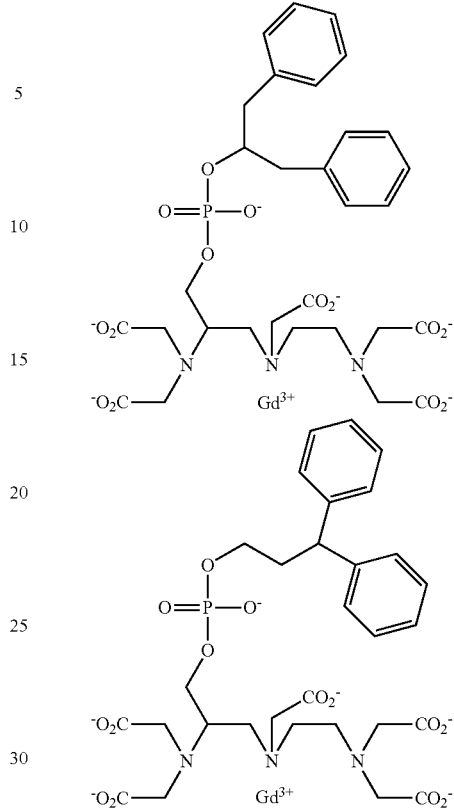

-continued or a pharmaceutically acceptable salt form thereof.

69. The method according to claim 57, wherein said imaging of said mammal comprises imaging a tumor of said mammal.

70. The method according to claim 57, wherein said imaging of said mammal comprises imaging the brain of said mammal.

71. The method according to claim 70, wherein said imaging of said brain comprises imaging the blood-brain barrier of said brain.

72. The method according to claim 70, wherein said imaging of said brain occurs when said mammal is undergoing cognitive events.

73. A method for examining vasculature of a tissue comprising HSA in a human, said method comprising:
  a) administering a diagnostic imaging contrast agent, or a pharmaceutically acceptable salt thereof, to said human, said diagnostic imaging contrast agent having the structure:

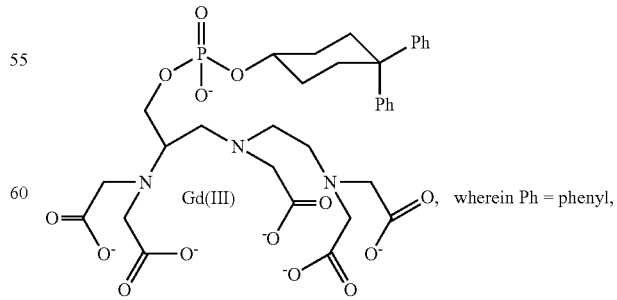

wherein Ph = phenyl, or a pharmaceutically acceptable salt thereof; and
  b) obtaining an MR image of said tissue.

74. The method of claim 73, wherein the pharmaceutically acceptable salt is selected from the group consisting of: N-methyl-D-glucamine, calcium, and sodium.

75. The method of claim 74, wherein the pharmaceutically acceptable salt is a trisodium salt.

76. A method for examining perfusion in a tissue comprising HSA in a human, said method comprising:
   a) administering a diagnostic imaging contrast agent, or a pharmaceutically acceptable salt thereof, to said human, said diagnostic imaging contrast agent having the structure:

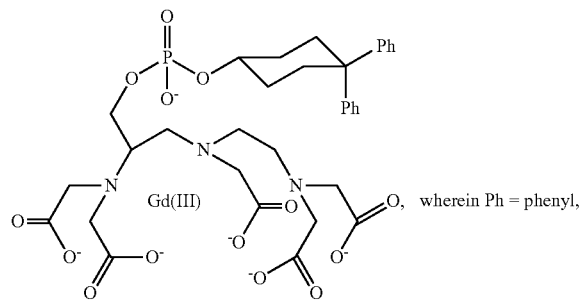

or a pharmaceutically acceptable salt thereof; and
   b) obtaining an MR image of said tissue of said human.

77. The method of claim 76, wherein the pharmaceutically acceptable salt is selected from the group consisting of: N-methyl-D-glucamine, calcium, and sodium.

78. The method of claim 77, wherein the pharmaceutically acceptable salt is a trisodium salt.

79. A method of monitoring a human's brain during cognitive events, said method comprising:
   a) administering a diagnostic imaging contrast agent, or a pharmaceutically acceptable salt thereof, to said human, said diagnostic imaging contrast agent having the structure:

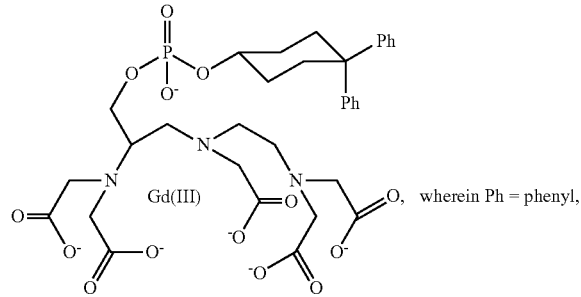

or a pharmaceutically acceptable salt thereof; and
   b) obtaining an MR image of said brain of said human.

80. The method of claim 79, wherein the pharmaceutically acceptable salt is selected from the group consisting of: N-methyl-D-glucamine, calcium, and sodium.

81. The method of claim 80, wherein the pharmaceutically acceptable salt is a trisodium salt.

82. A method for determining blood volume in a tissue comprising HSA in a human, said method comprising:
   a) administering a diagnostic imaging contrast agent, or a pharmaceutically acceptable salt thereof, to said human, said diagnostic imaging contrast agent having the structure:

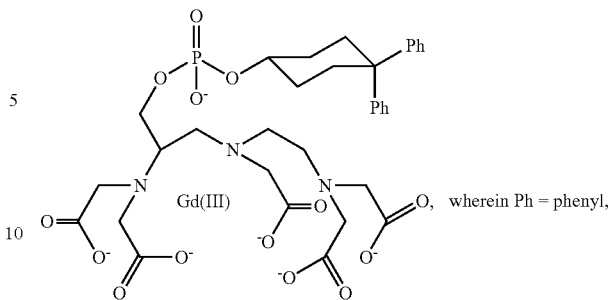

or a pharmaceutically acceptable salt thereof; and
   b) obtaining an MR image of said brain of said human.

83. The method of claim 82, wherein the pharmaceutically acceptable salt is selected from the group consisting of: N-methyl-D-glucamine, calcium, and sodium.

84. The method of claim 83, wherein the pharmaceutically acceptable salt is a trisodium salt.

85. A method of MR imaging of a mammal, said method comprising the steps of:
   a) administering to said mammal a diagnostic imaging contrast agent or a pharmaceutically acceptable salt thereof, said contrast agent having the structure:

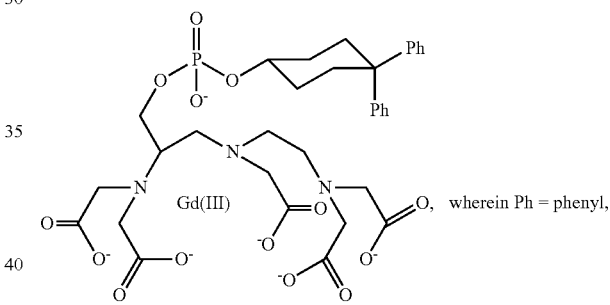

or a pharmaceutically acceptable salt thereof; and
   b) subjecting said mammal to MR imaging.

86. The method of claim 85, wherein the pharmaceutically acceptable salt is selected from the group consisting of: N-methyl-D-glucamine, calcium, and sodium.

87. The method of claim 86, wherein the pharmaceutically acceptable salt is a trisodium salt.

88. A method for examining vasculature of a tissue comprising HSA in a human, said method comprising:
   a) administering a diagnostic imaging contrast agent to said human, said diagnostic imaging contrast agent being a sodium salt having the following formula:

IEM-L-BHEM-PPBM, wherein PPBM is a plasma protein binding moiety, wherein the plasma protein is human serum albumin (HSA); wherein the PPBM has 7-18 carbon atoms and comprises at least 1 aryl ring selected from phenyl, naphthyl, biphenyl, and benzyl;
   wherein IEM is an image enhancing moiety and is selected from the following group:

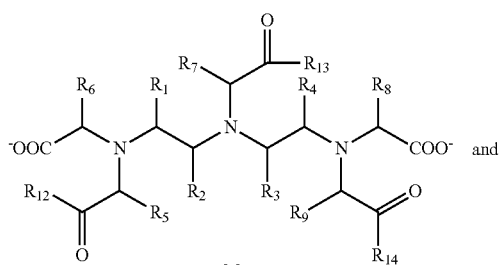

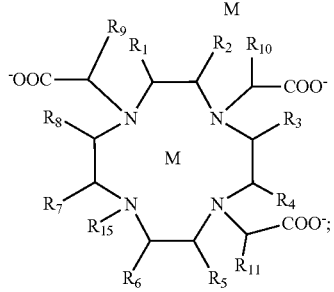

wherein one of $R_1$-$R_{11}$ is L-BHEM-PPBM and the $R_1$-$R_{11}$ groups that are not L-BHEM-PPBM are hydrogen;

wherein $R_{12}$, $R_{13}$, and $R_{14}$ can be the same or different and are selected from the group consisting of $O^-$ and $NH_2$;

wherein $R_{15}$ is H, $CH_2CH(OH)CH_3$, hydroxyl alkyl, or $CH_2COR_{12}$;

wherein said M is a paramagnetic metal ion chelated by the IEM and selected from the group consisting of Gd(III), Fe(III), Mn(II), Mn(III), Cr(III), Cu(II), Dy(III), Tb(III), Ho(III), Er(III), and Eu(III);

wherein L is a linker connecting the IEM to the BHEM consisting of 1 to 4 —$CH_2$— groups; and wherein the BHEM moiety is a blood half-life extending moiety and is a phosphodiester; and b) obtaining an MR image of said tissue.

89. A method for examining perfusion in a tissue comprising HSA in a human, said method comprising:

a) administering a diagnostic imaging contrast agent to said human, said diagnostic imaging contrast agent being a sodium salt having the following formula:

IEM-L-BHEM-PPBM, wherein PPBM is a plasma protein binding moiety, wherein the plasma protein is human serum albumin (HSA); wherein the PPBM has 7-18 carbon atoms and comprises at least 1 aryl ring selected from phenyl, naphthyl, biphenyl, and benzyl;

wherein IEM is an image enhancing moiety and is selected from the following group:

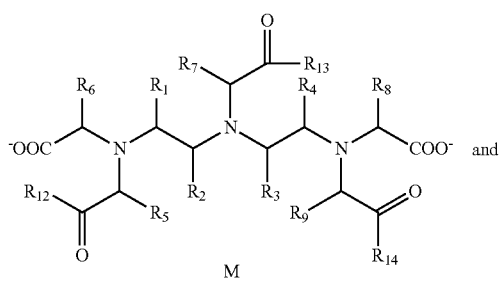

-continued

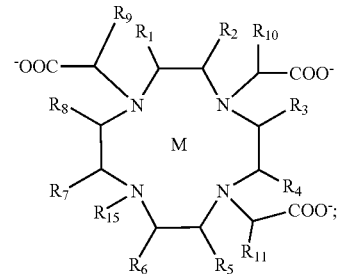

wherein one of $R_1$-$R_{11}$ is L-BHEM-PPBM and the $R_1$-$R_{11}$ groups that are not L-BHEM-PPBM are hydrogen;

wherein $R_{12}$, $R_{13}$, and $R_{14}$ can be the same or different and are selected from the group consisting of $O^-$ and $NH_2$;

wherein $R_{15}$ is H, $CH_2CH(OH)CH_3$, hydroxyl alkyl, or $CH_2COR_{12}$;

wherein said M is a paramagnetic metal ion chelated by the IEM and selected from the group consisting of Gd(III), Fe(III), Mn(II), Mn(III), Cr(III), Cu(II), Dy(III), Tb(III), Ho(III), Er(III), and Eu(III);

wherein L is a linker connecting the IEM to the BHEM consisting of 1 to 4 —$CH_2$— groups; and wherein the BHEM moiety is a blood half-life extending moiety and is a phosphodiester; and b) obtaining an MR image of said tissue of said human.

90. A method of monitoring a human's brain during cognitive events, said method comprising:

a) administering a diagnostic imaging contrast agent to said human, said diagnostic imaging contrast agent being a sodium salt having the following formula:

IEM-L-BHEM-PPBM, b) wherein PPBM is a plasma protein binding moiety, wherein the plasma protein is human serum albumin (HSA); wherein the PPBM has 7-18 carbon atoms and comprises at least 1 aryl ring selected from phenyl, naphthyl, biphenyl, and benzyl;

wherein IEM is an image enhancing moiety and is selected from the following group:

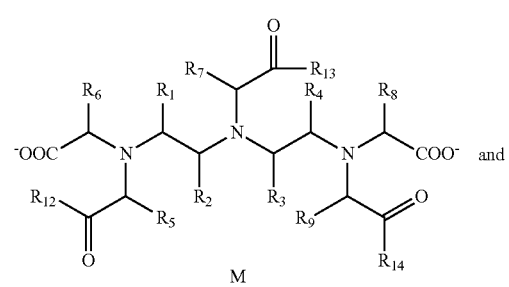

-continued

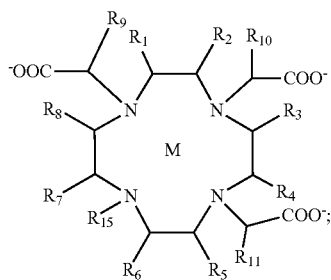

wherein one of $R_1$-$R_{11}$ is L-BHEM-PPBM and the $R_1$-$R_{11}$ groups that are not L-BHEM-PPBM are hydrogen;

wherein $R_{12}$, $R_{13}$, and $R_{14}$ can be the same or different and are selected from the group consisting of $O^-$ and $NH_2$;

wherein $R_{15}$ is H, $CH_2CH(OH)CH_3$, hydroxyl alkyl, or $CH_2COR_{12}$;

wherein said M is a paramagnetic metal ion chelated by the IEM and selected from the group consisting of Gd(III), Fe(III), Mn(II), Mn(III), Cr(III), Cu(II), Dy(III), Tb(III), Ho(III), Er(III), and Eu(III);

wherein L is a linker connecting the IEM to the BHEM consisting of 1 to 4 —$CH_2$— groups; and wherein the BHEM moiety is a blood half-life extending moiety and is a phosphodiester; and c) obtaining an MR image of said brain of said human.

91. A method for determining blood volume in a tissue comprising HSA in a human, said method comprising:

a) administering a diagnostic imaging contrast agent to said human, said diagnostic imaging contrast agent being a sodium salt having the following formula:

IEM-L-BHEM-PPBM, wherein PPBM is a plasma protein binding moiety, wherein the plasma protein is human serum albumin (HSA); wherein the PPBM has 7-18 carbon atoms and comprises at least 1 aryl ring selected from phenyl, naphthyl, biphenyl, and benzyl;

wherein IEM is an image enhancing moiety and is selected from the following group:

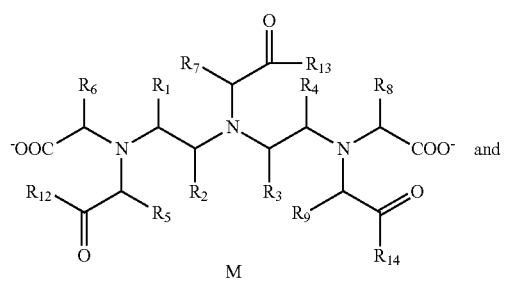 and

-continued

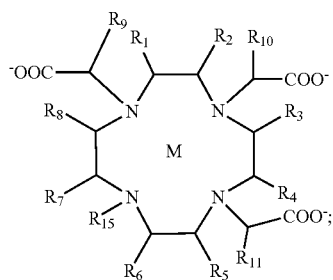

wherein one of $R_1$-$R_{11}$ is L-BHEM-PPBM and the $R_1$-$R_{11}$ groups that are not L-BHEM-PPBM are hydrogen;

wherein $R_{12}$, $R_{13}$, and $R_{14}$ can be the same or different and are selected from the group consisting of $O^-$ and $NH_2$;

wherein $R_{15}$ is H, $CH_2CH(OH)CH_3$, hydroxyl alkyl, or $CH_2COR_{12}$;

wherein said M is a paramagnetic metal ion chelated by the IEM and selected from the group consisting of Gd(III), Fe(III), Mn(II), Mn(III), Cr(III), Cu(II), Dy(III), Tb(III), Ho(III), Er(III), and Eu(III);

wherein L is a linker connecting the IEM to the BHEM consisting of 1 to 4 —$CH_2$— groups; and wherein the BHEM moiety is a blood half-life extending moiety and is a phosphodiester; and b) obtaining an MR image of said brain of said human.

92. A method of MR imaging of a mammal, said method comprising the steps of:

a) administering a diagnostic imaging contrast agent to said human, said diagnostic imaging contrast agent being a sodium salt having the following formula:

IEM-L-BHEM-PPBM, wherein PPBM is a plasma protein binding moiety, wherein the plasma protein is human serum albumin (HSA); wherein the PPBM has 7-18 carbon atoms and comprises at least 1 aryl ring selected from phenyl, naphthyl, biphenyl, and benzyl;

wherein IEM is an image enhancing moiety and is selected from the following group:

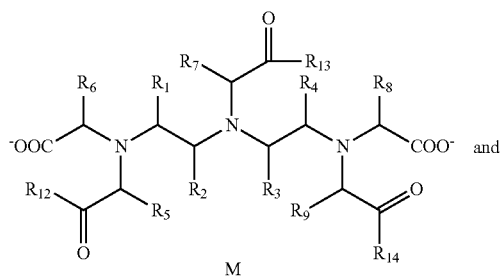 and

-continued

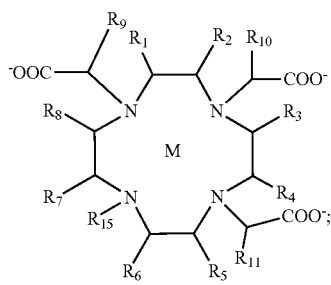

wherein one of $R_1$-$R_{11}$ is L-BHEM-PPBM and the $R_1$-$R_{11}$ groups that are not L-BHEM-PPBM are hydrogen;

wherein $R_{12}$, $R_{13}$, and $R_{14}$ can be the same or different and are selected from the group consisting of O$^-$ and NH$_2$;

wherein $R_{15}$ is H, CH$_2$CH(OH)CH$_3$, hydroxyl alkyl, or CH$_2$COR$_{12}$;

wherein said M is a paramagnetic metal ion chelated by the IEM and selected from the group consisting of Gd(III), Fe(III), Mn(II), Mn(III), Cr(III), Cu(II), Dy(III), Tb(III), Ho(III), Er(III), and Eu(III);

wherein L is a linker connecting the IEM to the BHEM consisting of 1 to 4 —CH$_2$— groups; and wherein the BHEM moiety is a blood half-life extending moiety and is a phosphodiester; and b) subjecting said mammal to MR imaging.

93. A method for examining vasculature of a tissue comprising HSA in a human, said method comprising:

a) administering a diagnostic imaging contrast agent to said human, said diagnostic imaging contrast agent being a sodium salt having the structure:

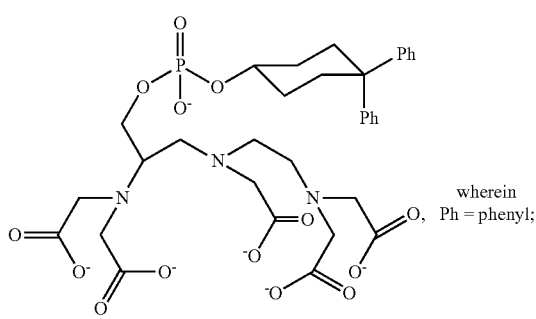

wherein Ph = phenyl;

and b) obtaining an MR image of said tissue.

94. A method for examining perfusion in a tissue comprising HSA in a human, said method comprising:

a) administering a diagnostic imaging contrast agent to said human, said diagnostic imaging contrast agent being a sodium salt having the structure:

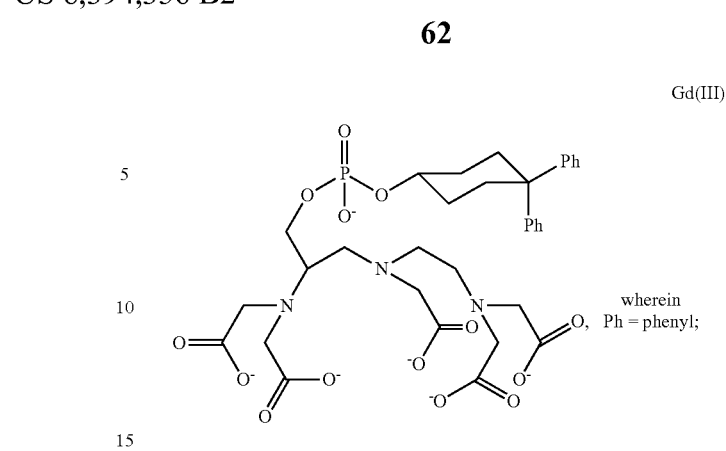

wherein Ph = phenyl;

and b) obtaining an MR image of said tissue of said human.

95. A method of monitoring a human's brain during cognitive events, said method comprising:

a) administering a diagnostic imaging contrast agent to said human, said diagnostic imaging contrast agent being a sodium salt having the structure:

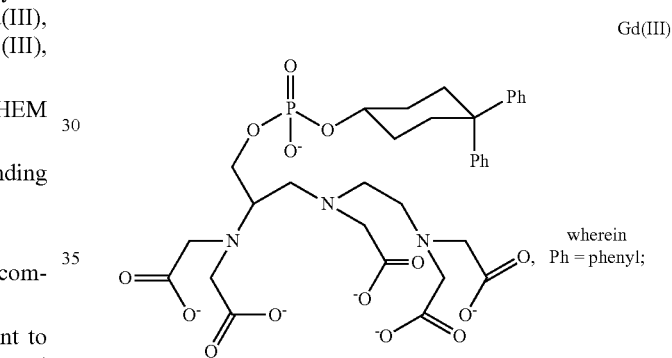

wherein Ph = phenyl;

and b) obtaining an MR image of said brain of said human.

96. A method for determining blood volume in a tissue comprising HSA in a human, said method comprising:

a) administering a diagnostic imaging contrast agent to said human, said diagnostic imaging contrast agent being a sodium salt having the structure:

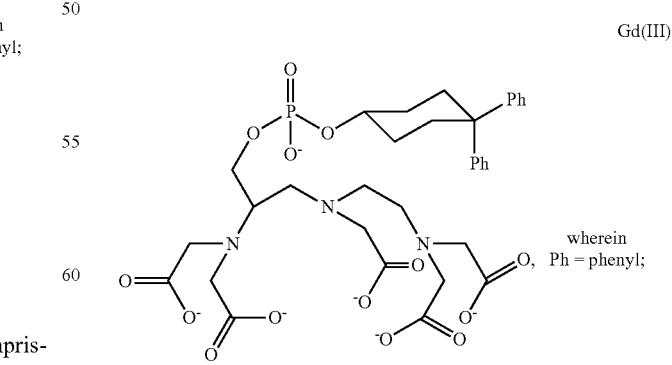

wherein Ph = phenyl;

and b) obtaining an MR image of said brain of said human.

97. A method of MR imaging of a mammal, said method comprising the steps of:
a) administering a diagnostic imaging contrast agent to said human, said diagnostic imaging contrast agent being a sodium salt having the structure:

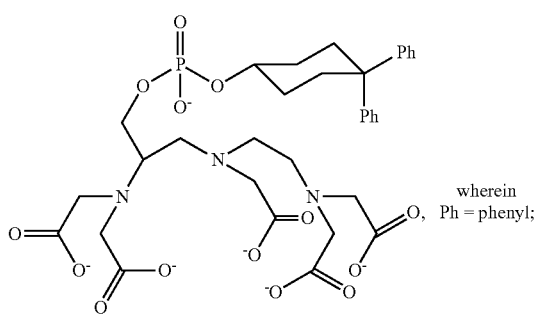

wherein Ph = phenyl;

and
b) subjecting said mammal to MR imaging.

98. A method for examining vasculature of a tissue comprising HSA in a human, said method comprising:
a) administering a diagnostic imaging contrast agent to said human, said diagnostic imaging contrast agent being a trisodium salt having the following formula:

IEM-L-BHEM-PPBM, wherein PPBM is a plasma protein binding moiety, wherein the plasma protein is human serum albumin (HSA); wherein the PPBM has 7-18 carbon atoms and comprises at least 1 aryl ring selected from phenyl, naphthyl, biphenyl, and benzyl;

wherein IEM is an image enhancing moiety and is selected from the following group:

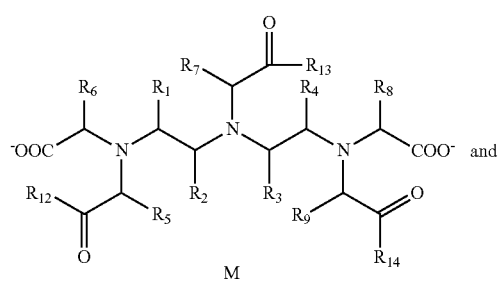

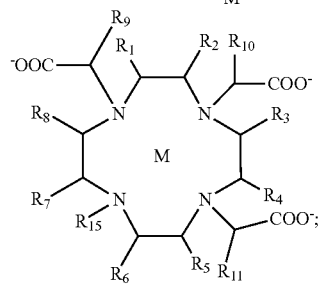

wherein one of $R_1$-$R_{11}$ is L-BHEM-PPBM and the $R_1$-$R_{11}$ groups that are not L-BHEM-PPBM are hydrogen;

wherein $R_{12}$, $R_{13}$, and $R_{14}$ can be the same or different and are selected from the group consisting of $O^-$ and $NH_2$;

wherein $R_{15}$ is H, $CH_2CH(OH)CH_3$, hydroxyl alkyl, or $CH_2COR_{12}$;

wherein said M is a paramagnetic metal ion chelated by the IEM and selected from the group consisting of Gd(III), Fe(III), Mn(II), Mn(III), Cr(III), Cu(II), Dy(III), Tb(III), Ho(III), Er(III), and Eu(III);

wherein L is a linker connecting the IEM to the BHEM consisting of 1 to 4 —$CH_2$— groups; and wherein the BHEM moiety is a blood half-life extending moiety and is a phosphodiester; and b) obtaining an MR image of said tissue.

99. A method for examining perfusion in a tissue comprising HSA in a human, said method comprising:
a) administering a diagnostic imaging contrast agent to said human, said diagnostic imaging contrast agent being a trisodium salt having the following formula:

IEM-L-BHEM-PPBM, wherein PPBM is a plasma protein binding moiety, wherein the plasma protein is human serum albumin (HSA); wherein the PPBM has 7-18 carbon atoms and comprises at least 1 aryl ring selected from phenyl, naphthyl, biphenyl, and benzyl;

wherein IEM is an image enhancing moiety and is selected from the following group:

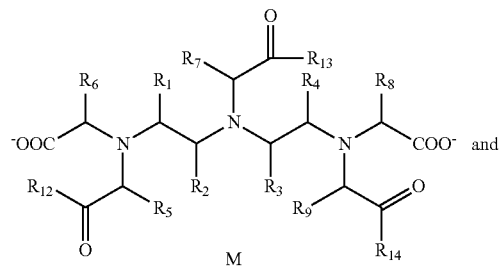

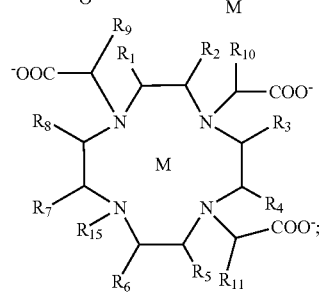

wherein one of $R_1$-$R_{11}$ is L-BHEM-PPBM and the $R_1$-$R_{11}$ groups that are not L-BHEM-PPBM are hydrogen;

wherein $R_{12}$, $R_{13}$, and $R_{14}$ can be the same or different and are selected from the group consisting of $O^-$ and $NH_2$;

wherein $R_{15}$ is H, $CH_2CH(OH)CH_3$, hydroxyl alkyl, or $CH_2COR_{12}$;

wherein said M is a paramagnetic metal ion chelated by the IEM and selected from the group consisting of Gd(III), Fe(III), Mn(II), Mn(III), Cr(III), Cu(II), Dy(III), Tb(III), Ho(III), Er(III), and Eu(III);

wherein L is a linker connecting the IEM to the BHEM consisting of 1 to 4 —$CH_2$— groups; and wherein the BHEM moiety is a blood half-life extending moiety and is a phosphodiester; and b) obtaining an MR image of said tissue of said human.

100. A method of monitoring a human's brain during cognitive events, said method comprising:
a) administering a diagnostic imaging contrast agent to said human, said diagnostic imaging contrast agent being a trisodium salt having the following formula:

IEM-L-BHEM-PPBM, b) wherein PPBM is a plasma protein binding moiety, wherein the plasma protein is human serum albumin (HSA); wherein the PPBM has 7-18 carbon atoms and comprises at least 1 aryl ring selected from phenyl, naphthyl, biphenyl, and benzyl;
wherein IEM is an image enhancing moiety and is selected from the following group:

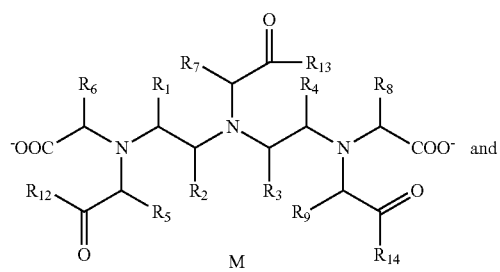

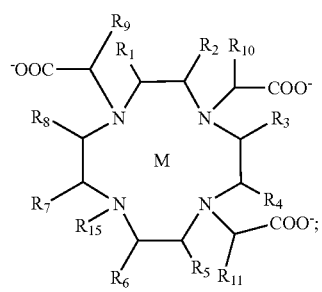

wherein one of $R_1$-$R_{11}$ is L-BHEM-PPBM and the $R_1$-$R_{11}$ groups that are not L-BHEM-PPBM are hydrogen;
wherein $R_{12}$, $R_{13}$, and $R_{14}$ can be the same or different and are selected from the group consisting of $O^-$ and $NH_2$;
wherein $R_{15}$ is H, $CH_2CH(OH)CH_3$, hydroxyl alkyl, or $CH_2COR_{12}$;
wherein said M is a paramagnetic metal ion chelated by the IEM and selected from the group consisting of Gd(III), Fe(III), Mn(II), Mn(III), Cr(III), Cu(II), Dy(III), Tb(III), Ho(III), Er(III), and Eu(III);
wherein L is a linker connecting the IEM to the BHEM consisting of 1 to 4 —$CH_2$— groups; and
wherein the BHEM moiety is a blood half-life extending moiety and is a phosphodiester; and
c) obtaining an MR image of said brain of said human.

101. A method for determining blood volume in a tissue comprising HSA in a human, said method comprising:
a) administering a diagnostic imaging contrast agent to said human, said diagnostic imaging contrast agent being a trisodium salt having the following formula:

IEM-L-BHEM-PPBM, wherein PPBM is a plasma protein binding moiety, wherein the plasma protein is human serum albumin (HSA); wherein the PPBM has 7-18 carbon atoms and comprises at least 1 aryl ring selected from phenyl, naphthyl, biphenyl, and benzyl;
wherein IEM is an image enhancing moiety and is selected from the following group:

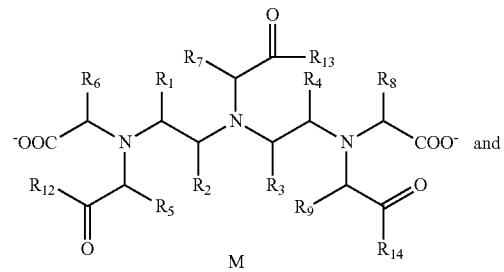

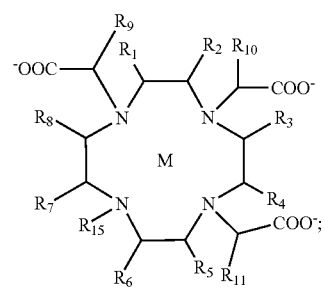

wherein one of $R_1$-$R_{11}$ is L-BHEM-PPBM and the $R_1$-$R_{11}$ groups that are not L-BHEM-PPBM are hydrogen;
wherein $R_{12}$, $R_{13}$, and $R_{14}$ can be the same or different and are selected from the group consisting of $O^-$ and $NH_2$;
wherein $R_{15}$ is H, $CH_2CH(OH)CH_3$, hydroxyl alkyl, or $CH_2COR_{12}$;
wherein said M is a paramagnetic metal ion chelated by the IEM and selected from the group consisting of Gd(III), Fe(III), Mn(II), Mn(III), Cr(III), Cu(II), Dy(III), Tb(III), Ho(III), Er(III), and Eu(III);
wherein L is a linker connecting the IEM to the BHEM consisting of 1 to 4 —$CH_2$— groups; and
wherein the BHEM moiety is a blood half-life extending moiety and is a phosphodiester; and
b) obtaining an MR image of said brain of said human.

102. A method of MR imaging of a mammal, said method comprising the steps of:
a) administering a diagnostic imaging contrast agent to said human, said diagnostic imaging contrast agent being a trisodium salt having the following formula:

IEM-L-BHEM-PPBM, wherein PPBM is a plasma protein binding moiety, wherein the plasma protein is human serum albumin (HSA); wherein the PPBM has 7-18 carbon atoms and comprises at least 1 aryl ring selected from phenyl, naphthyl, biphenyl, and benzyl;

wherein IEM is an image enhancing moiety and is selected from the following group:

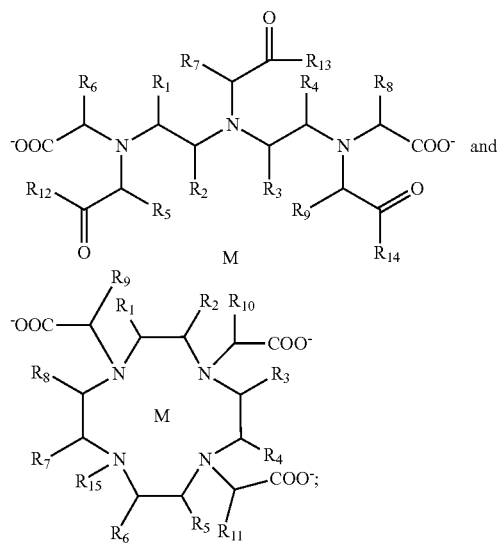

wherein one of $R_1$-$R_{11}$ is L-BHEM-PPBM and the $R_1$-$R_{11}$ groups that are not L-BHEM-PPBM are hydrogen;

wherein $R_{12}$, $R_{13}$, and $R_{14}$ can be the same or different and are selected from the group consisting of $O^-$ and $NH_2$;

wherein $R_{15}$ is H, $CH_2CH(OH)CH_3$, hydroxyl alkyl, or $CH_2COR_{12}$;

wherein said M is a paramagnetic metal ion chelated by the IEM and selected from the group consisting of Gd(III), Fe(III), Mn(II), Mn(III), Cr(III), Cu(II), Dy(III), Tb(III), Ho(III), Er(III), and Eu(III);

wherein L is a linker connecting the IEM to the BHEM consisting of 1 to 4 —$CH_2$— groups; and wherein the BHEM moiety is a blood half-life extending moiety and is a phosphodiester; and b) subjecting said mammal to MR imaging.

103. A method for examining vasculature of a tissue comprising HSA in a human, said method comprising:

a) administering a diagnostic imaging contrast agent to said human, said diagnostic imaging contrast agent being a trisodium salt having the structure:

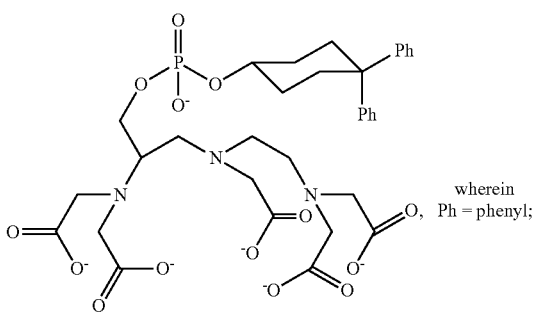

and
b) obtaining an MR image of said tissue.

104. A method for examining perfusion in a tissue comprising HSA in a human, said method comprising:

a) administering a diagnostic imaging contrast agent to said human, said diagnostic imaging contrast agent being a trisodium salt having the structure:

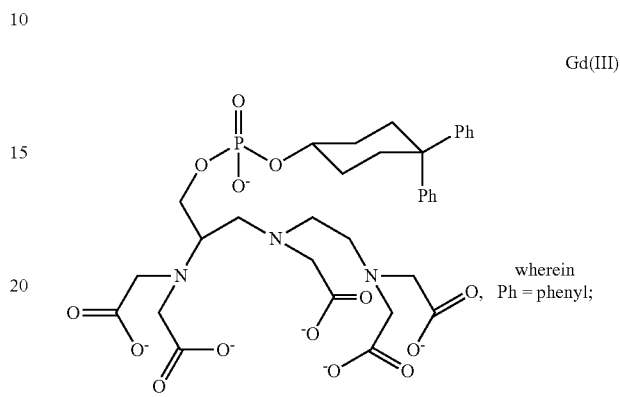

and
b) obtaining an MR image of said tissue of said human.

105. A method of monitoring a human's brain during cognitive events, said method comprising:

a) administering a diagnostic imaging contrast agent to said human, said diagnostic imaging contrast agent being a trisodium salt having the structure:

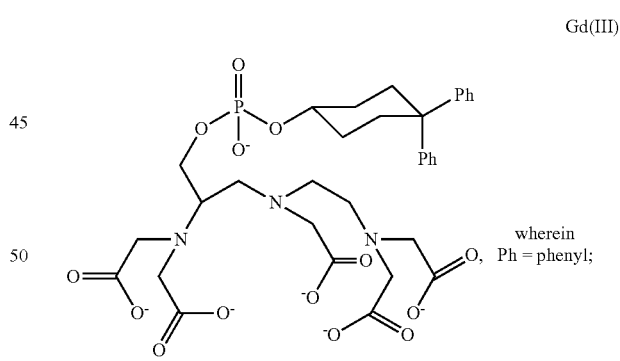

and
b) obtaining an MR image of said brain of said human.

106. A method for determining blood volume in a tissue comprising HSA in a human, said method comprising:

a) administering a diagnostic imaging contrast agent to said human, said diagnostic imaging contrast agent being a trisodium salt having the structure:

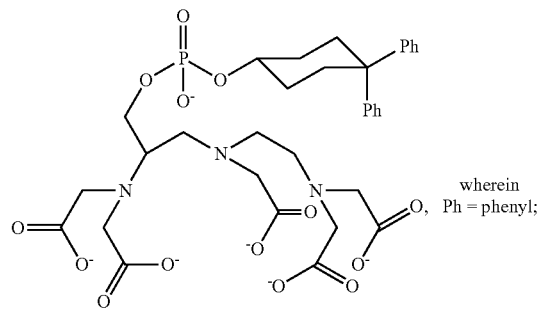
wherein Ph = phenyl;
and
b) obtaining an MR image of said brain of said human.
107. A method of MR imaging of a mammal, said method comprising the steps of:
a) administering a diagnostic imaging contrast agent to said human, said diagnostic imaging contrast agent being a trisodium salt having the structure:
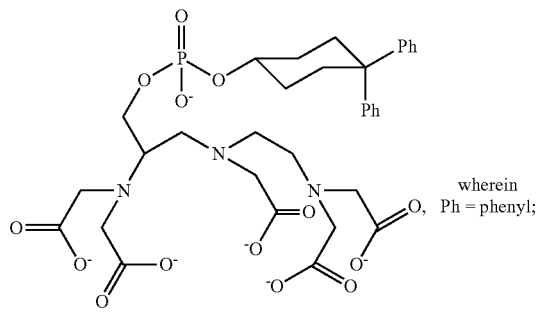
wherein Ph = phenyl;
and
b) subjecting said mammal to MR imaging.
* * * * *

UNITED STATES PATENT AND TRADEMARK OFFICE
CERTIFICATE OF CORRECTION

PATENT NO.       : 8,394,356 B2
APPLICATION NO.  : 13/220103
DATED            : March 12, 2013
INVENTOR(S)      : Thomas J. McMurry It is certified that error appears in the above-identified patent and that said Letters Patent is hereby corrected as shown below:

Title Page, Item (56);
Column 2, Other Publications, line 3, please delete "alky-lenediamineacetic" and insert --alkylenediamineacetic--, therefor;

Column 2, Other Publications, line 7, please delete "(βImino" and insert --αImino--, therefor;

In the Claims
Column 37, line 51 (Claim 10), delete "mmnol/kg" and insert --mmol/kg--, therefor;

Column 41, line 37 (Claim 25), delete "mmnol/kg" and insert --mmol/kg--, therefor;

Column 45, line 13 (Claim 40), delete "mmnol/kg" and insert --mmol/kg--, therefor;

Column 48, line 64 (Claim 51), delete "mmnol/kg" and insert --mmol/kg--, therefor;

Column 51, lines 42-49 (Claim 58), delete " 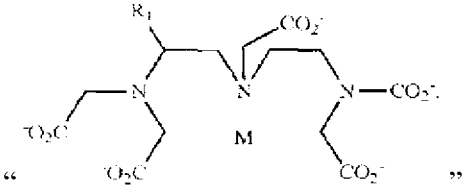 "

and insert -- 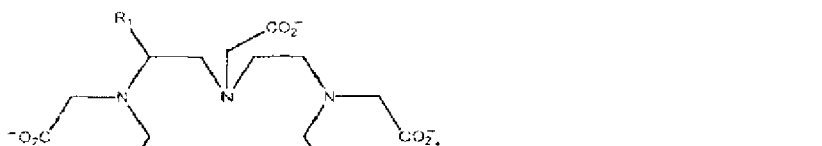 --, therefor;

Column 52, lines 63-64 (Claim 67), delete "mmnol/kg" and insert --mmol/kg--, therefor.

Signed and Sealed this
Twenty-eighth Day of May, 2013

Teresa Stanek Rea
*Acting Director of the United States Patent and Trademark Office*